US012173004B2

(12) United States Patent
Li et al.

(10) Patent No.: US 12,173,004 B2
(45) Date of Patent: *Dec. 24, 2024

(54) PHARMACEUTICAL COMPOSITIONS COMPRISING HETEROCYCLE FUSED GAMMA CARBOLINE PRODRUGS

(71) Applicant: INTRA-CELLULAR THERAPIES, INC., New York, NY (US)

(72) Inventors: Peng Li, New Milford, NJ (US); Hailin Zheng, New York, NY (US); Robert Davis, San Diego, CA (US); Sharon Mates, New York, NY (US); Kimberly Vanover, New York, NY (US); Gretchen Snyder, New York, NY (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/451,465

(22) Filed: Aug. 17, 2023

(65) Prior Publication Data
US 2024/0059687 A1    Feb. 22, 2024

Related U.S. Application Data

(60) Continuation of application No. 17/813,473, filed on Jul. 19, 2022, now Pat. No. 11,773,095, which is a division of application No. 16/634,059, filed as application No. PCT/US2018/043102 on Jul. 20, 2018, now Pat. No. 11,427,587.

(60) Provisional application No. 62/647,492, filed on Mar. 23, 2018, provisional application No. 62/537,292, filed on Jul. 26, 2017.

(51) Int. Cl.
| | | |
|---|---|---|
| *A61K 31/4985* | (2006.01) | |
| *A61K 45/06* | (2006.01) | |
| *A61P 1/00* | (2006.01) | |
| *A61P 11/00* | (2006.01) | |
| *A61P 25/36* | (2006.01) | |
| *A61P 29/00* | (2006.01) | |
| *C07D 471/16* | (2006.01) | |

(52) U.S. Cl.
CPC ............ *C07D 471/16* (2013.01); *A61K 45/06* (2013.01); *A61P 1/00* (2018.01); *A61P 11/00* (2018.01); *A61P 25/36* (2018.01); *A61P 29/00* (2018.01)

(58) Field of Classification Search
CPC ............... C07D 471/16; C07D 471/18; C07D 471/14; A61K 45/06; A61K 31/137; A61K 31/485; A61K 31/4985; A61K 31/5383; A61K 31/55; A61K 9/0019; A61K 2300/00; A61P 1/00; A61P 11/00; A61P 25/36; A61P 29/00; A61P 25/00; A61P 3/04; A61P 25/04; A61P 25/06; A61P 25/16; A61P 25/18; A61P 25/22; A61P 25/24; A61P 25/28; A61P 25/30; A61P 25/32

USPC ........................................................ 514/250
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 4,001,263 A | 1/1977 | Plattner et al. |
| 4,136,145 A | 1/1979 | Fuchs et al. |
| 4,219,550 A | 8/1980 | Rajagopalan |
| 4,238,607 A | 12/1980 | Rajagopalan |
| 4,389,330 A | 6/1983 | Tice et al. |
| 4,530,840 A | 7/1985 | Tice et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,235,936 B1 | 5/2001 | Buchwald et al. |
| 6,307,087 B1 | 10/2001 | Buchwald et al. |

(Continued)

FOREIGN PATENT DOCUMENTS

| | | |
|---|---|---|
| GB | 1476087 | 6/1977 |
| WO | WO 2000/064899 | 11/2000 |

OTHER PUBLICATIONS

Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.

Alvir, et al. Clozapine-Induced Agranulocytosis. The New England Journal of Medicine, 1993, vol. 329, No. 3, pp. 162-167.

Angst et al. "Prevalence and Characteristics of Undiagnosed Bipolar Disorders in Patients With a Major Depressive Episode", Arch Gen Psychiatry, vol. 68(8), p. 701-709, (2011).

(Continued)

*Primary Examiner* — Taylor V Oh
(74) *Attorney, Agent, or Firm* — Hoxie & Associates LLC

(57) ABSTRACT

The invention relates to particular prodrugs of substituted heterocycle fused gamma-carbolines, in free, solid, pharmaceutically acceptable salt and/or substantially pure form as described herein, pharmaceutical compositions thereof, and methods of use in the treatment of diseases involving the 5-HT$_{2A}$ receptor, the serotonin transporter (SERT), pathways involving the dopamine $D_1$ and $D_2$ receptor signaling system, and/or the μ-opioid receptor.

24 Claims, No Drawings

(56) References Cited

U.S. PATENT DOCUMENTS

| | | |
|---|---|---|
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,888,032 B2 | 5/2005 | Buchwald et al. |
| 7,071,186 B2 | 7/2006 | Robichaud et al. |
| 7,081,455 B2 | 7/2006 | Robichaud et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 8,309,722 B2 | 11/2012 | Tomesch et al. |
| 8,461,148 B2 | 6/2013 | Hollander |
| 8,598,119 B2 | 12/2013 | Mates et al. |
| 8,603,514 B2 | 12/2013 | Yang et al. |
| 8,648,077 B2 | 2/2014 | Tomesch et al. |
| 8,779,139 B2 | 7/2014 | Tomesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,118,926 B2 | 11/2018 | Koolman et al. |
| 10,179,776 B2 | 1/2019 | Davis et al. |
| 10,221,176 B2 | 3/2019 | Tomesch et al. |
| 10,245,260 B2 | 4/2019 | Yao et al. |
| 10,322,134 B2 | 7/2019 | Vanover et al. |
| 10,363,220 B2 | 7/2019 | Li |
| 10,472,359 B2 | 11/2019 | Li et al. |
| 10,533,015 B1 | 1/2020 | Tusche et al. |
| 10,597,394 B2 | 3/2020 | Yao et al. |
| 10,597,395 B2 | 3/2020 | Tomesch et al. |
| 10,654,854 B2 | 5/2020 | Li et al. |
| 10,682,354 B2 | 6/2020 | Wennogle |
| 10,688,097 B2 | 6/2020 | Yao et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Mates et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 | 6/2021 | Mates et al. |
| 11,052,083 B2 | 7/2021 | Li et al. |
| 11,053,245 B2 | 7/2021 | Mates et al. |
| 11,096,944 B2 | 8/2021 | Yao et al. |
| 11,124,514 B2 | 9/2021 | Mates et al. |
| 11,332,469 B2 | 5/2022 | Mittelman et al. |
| 11,376,249 B2 | 7/2022 | Li et al. |
| 11,427,587 B2 * | 8/2022 | Li .......................... A61K 31/485 |
| 11,773,095 B2 * | 10/2023 | Li .......................... A61P 25/36 514/250 |
| 11,844,757 B2 | 12/2023 | Yao et al. |
| 11,958,852 B2 | 4/2024 | Mates et al. |
| 12,023,331 B2 | 7/2024 | Snyder et al. |
| 2004/0142970 A1 | 7/2004 | Chung et al. |
| 2005/0222209 A1 | 10/2005 | Zeldis et al. |
| 2008/0132552 A1 | 6/2008 | Kleinman et al. |
| 2008/0287450 A1 | 11/2008 | Cid-Nunez et al. |
| 2015/0374684 A1 | 12/2015 | Javitt |
| 2020/0392135 A1 | 12/2020 | Wennogle et al. |
| 2021/0008065 A1 | 1/2021 | Li et al. |
| 2021/0009592 A1 | 1/2021 | Li et al. |
| 2022/0048910 A1 | 2/2022 | Li et al. |
| 2022/0056030 A1 | 2/2022 | Li et al. |
| 2022/0056031 A1 | 2/2022 | Li et al. |
| 2022/0160704 A2 | 5/2022 | Torralva |
| 2022/0184072 A1 | 6/2022 | Davis et al. |

OTHER PUBLICATIONS

Avendano, C., et al., "The problem of the existence of C(Ar)-H . . . N Intramolecular Hydrogen Bonds in a Family of 9-Azaphenyl-9H-carbazoles," J. Chem. Soc. Perkin Trans., vol. 2, pp. 1547-1555, (1993).

Balbach, S., et al., "Pharmaceutical evaluation of early development candidates 'the 100 mg-approach'", International Journal of Pharmaceutics, vol. 275, p. 1-12 (2004).

Bastin, R., et al.,"Salt Selection and Optimisation Procedures for Pharmaceutical New Chemical Entities", Organic Process and Research Development, vol. 4, No. 5, pp. 427-435 (2000).

Beletskaya, I.P., et al., "Pd- and Cu-catalyzed selective arylation of benzotriazole," Tetrahedron Letters, vol. 39, pp. 5617-5620, (1998).

Berger, J., et al., "Synthesis of some conformationally restricted analogs of fentanyl." Journal of Medicinal Chemistry, vol. 20, No. 4, p. 600-602. 1977.

Bobo, et al., "Fluoxetine and olanzapine combination therapy in treatment-resistant major depression: review of efficacy and safety data", Expert Opinion on Pharmacotherapy, 10(13), pp. 2145-2159, (2009).

Boger, D., et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System" J. Org. Chem., vol. 50, p. 5782-5789, (1985).

Borghans, et al., "Animal Models for Posttraumatic Stress Disorder: An Overview of What is Used in Research," World J. Psychiatr., vol. 5, No. 4, pp. 387-396, (2015); DOI: 10.5498/wjp.v5.14.387.

Bowman, W.R., et al., "Copper (1) Catalysed Aromatic Nucleophilic Substitution: A Mechanistic and Synthetic Comparison with the SRN 1 Reaction", Tetrahedron Letters, vol. 25(50) p. 5821-5824, (1984).

Bowman, W.R., et al., "Intramolecular Aromatic Substitution (SRN1) Reactions—Use of Entrainment for the Preparation of Benzothiazoles," Tetrahedron Letters, vol. 23, pp. 5093-5096, (1982).

Bowman, W.R., et al.,"Synthesis of 1H-quinazoline-4-ones using intramolecular aromatic nucelophilic substitution," ARKIVOC, vol. x, pp. 434-442 (2003).

Bremner et al., "Neuroimaging of Posttraumatic Stress Disorder", Psychiatric Annals Journal, vol. 28, Issue 8, p. 445-450, (1998).

Bryan-Lluka, L. J. et al., "Potencies of haloperidol metabolites as inhibitors of the human noradrenaline, dopamine and serotonin transporters in transfected COS-7 cells", Naunyn-Shemiedeberg's Arch Pharmacol, 1999, vol. 360, pp. 109-115.

Byrn, S., et al., "Pharmaceutical Solids: A Strategic Approach to Regulatory Considerations", Pharmaceutical Research, vol. 12, No. 7, p. 945-954 (1995).

Centers for Disease Control and Prevention [Online]. "Prevent Opioid Use Disorder". [Retrieved Dec. 9, 2021]. Retrieved from the Internet: <URL: https://www.cdc.gov/opioids/overdoseprevention/opioid-use-disorder.html>. Published Oct. 11, 2017. One Page . (Year: 2017).

(56) References Cited

OTHER PUBLICATIONS

Crawford, K., et al., "Copper-Catalyzed amidations of bromo substituted furans and thiophenes", Tetrahedron Letters, vol. 43, p. 7365-7368, (2002).
Darmani, N. A., et al., "Do Functional Relationships Exist Between 5-HT1A and 5-HT2 Receptors?," Pharmacology and Biochemistry & Behavior, vol. 36, p. 901-906, (1990).
Davis et al., "ITI-007 in the treatment of schizophrenia: from novel pharmacology to clinical outcomes," Expert Review of Neurotherapeutics, vol. 16, No. 6, pp. 601-614 (2016).
Davis, et al. "ITI-007 demonstrates brain occupancy at serotonin 5-HT2A and dopamine D2 receptors and serotonin transporters using positron emission tomography in healthy volunteers", Psychopharmacology, vol. 232:2863-2872,(2015).
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.
Dutheil, et al., "Lumateperone Normalizes Pathological Levels of Acute Inflammation through Important Pathways Known to Be Involved in Mood Regulation", *The Journal of Neuroscience*, 43(5), pp. 863-877, (2023).
Evindar, G., et al., "Copper- and Palladium-Catalyzed Intramolecular Aryl Guanidinylation: An Efficient Method for the Synthesis of 2-Aminobenzimidazoles", Organic Letters, vol. 5, No. 2, p. 133-136, (2003).
Ezquerra, J., et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).
Fawcett, J., "Posttraumatic Stress Disorder, Stress, and Happiness", Psychiatric Annals Journal, vol. 28, Issue 8, p. 427-428, (1998).
Fee, W.W., et al., "Copper (II)-promoted solvolyses of nickel (II) complexes III. Tetradentate Schiff base ligands containing various diamine segments," Aust. J. Chem., vol. 26, pp. 1475-1485, (1973).
Ferreira, I., et al., "Novel synthetic routes to thienocarbazoles via palladium or copper catalyzed amination or amidation of arylhalides and intramolecular cyclization", Tetrahedron, vol. 58, p. 7943-7949, (2002).
Finet, J-P., et al., "Recent advances in ullmann reaction: copper (II) diacetate catalysed N-, )- and S-arylation involving polycoordinate heteroatomic derivatives," Current Organic Chemistry, vol. 6, pp. 597-626, (2002).
Foster, P.S., et al., "Acetylcholinesterase inhibitors reduce spreading activation in dementia," Neuropsychologia, vol. 50, p. 2093-2099, (2012).
Friedman, M.J.., "Current and Future Drug Treatment for Posttraumatic Stress Disorder Patients", Psychiatric Annals Journal, vol. 28, Issue 8, p. 464-468, (1998).
Goodbrand, H.B., et al., "Ligand-Accelerated catalysis of the Ullmann condensation: Application to hole conducting triarylamines," J. Org. Chem., vol. 64, pp. 670-674, (1999).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Grant, D., "Theory and Origin and Polymorphism", Polymorphism in Pharmaceutical Solids, Chapter 1, p. 1-10 (1999).
Guillory, J.K., "Generation of Polymorphs, Hydrates, Solvates, and Amorphous Solids", Polymorphism in Pharmaceutical Solids, Chapter 5, p. 183-226 (1999).
Hackam, D., et al., "Translation of Research Evidence from Animals to Humans", JAMA, vol. 296, No. 14, p. 1731-1732 (2006).
Hamann, B., et al., "Systematic Variation of Bidentate Ligands used in Aryl Halide Amination. Unexpected Effects of Steric, Electronic, and Geometric Perturbations", J. Am. Chem. Soc., vol. 120, p. 3694-3703, (1998).
Harbert, C.A. et al., "Neuroleptic Activity in 5-Aryltetrahydro-y-carbolines", J. Med. Chem, vol. 23, p. 635-643 (1980).

Hartwig, J., "Palladium-catalyzed amination of aryl halides: Mechanism and rational catalyst design," Synlett, pp. 1212-329-340, (1996).
Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).
Hassan, J., et al., "Aryl-aryl bond formation one century after the discovery of the ullrnann reaction," Chem. Rev., vol. 102, pp. 1359-1469, (2002).
Haynes, et al., "Occurrence of Pharmaceutically Acceptable Anions and Cations in the Cambridge Structural Database", Journal of Pharmaceutical Sciences, vol. 94, No. 10, p. 2111-2120 (2005).
Hlavinka, E., "Schizophrenia Tx Eases Depression in Bipolar Disorder: Lumateperone Offers Greater Rate of Response, Remission versus Placebo," Medpage Today, 7 pages, (2020).
Intra-Cellular Therapies, Inc., "Corporate Presentation" (Sep. 24, 2019), downloaded from https://ir.intracellulartherapies.com/static-files/93b08960-f01c-4864-aa22-80adb3539753 (last accessed Mar. 13, 2023).
Ito, T., et al., "Studies of organic catalytic reactions. VI. The function of pyridine and copper in the Rosenrnund-von Braun reaction," Bulletin of the Chemical Society of Japan vol. 41, pp. 419-423, (1968).
Izrayelit, L., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy," Indian Drugs, vol. 23, No. 6, pp. 315-316 (1986).
Ji, J., et al., "Selective amination of polyhalopyridines catalyzed by a palladium-xantphos complex," Organic Letters, vol. 5, No. 24, pp. 4611-4614, (2003).
Jordan, V.C., "Tamoxifen: A Most Unlikely Pioneering Medicine", Nature Reviews: Drug Discovery, vol. 2, p. 205-213, (2003).
Kametani, T., et al., "A Novel Synthesis of Indole Derivatives", Heterocycles, vol. 14, No. 3, p. 277-280, (1980).
Kang, S-K., et al., "Copper-catalyzed N-arylation of aryl iodides with benzamides or nitrogen heterocycles in the presence of ethylendiamine," Synlett, No. 3, pp. 427-430, (2002).
Kay, S.R., et al., "The Positive and Negative Syndrome Scale (PANSS) for Schizophrenia," Schizophrenia Bulletin, vol. 13, Issue 2, pp. 261-276, (1987).
Kessler, R.C., et al., "Lifetime Prevalence and Age-of-Onset Distributions of DSM-IV Disorders in the National Comorbidity Survey Replication", Arch Gen Psychiatry; vol. 62, p. 593-602, (2005).
Khorana, N., et al., "Gamma-Carbolines: Binding at 5-HT5A Serotonin Receptors", Bioorganic & Medicinal Chemistry, vol. 11, pp. 717-722, p. 718 Table 1, (2003).
Kiyomori, A., et al., "An efficient copper-catalyzed coupling of aryl halides with imidazoles," Tetrahedron Letters, vol. 40, pp. 2657-2660, (1999).
Klapars, A., et al., "A general and efficient copper catalyst for the amidation of aryl halides and the N-arylation of nitrogen heterocycles," J. Am. Chem. Soc., vol. 123, pp. 7727-7729, (2001).
Klapars, A., et al., "A general and efficient copper catalyst for the amidation of aryl halides," J. Am. Chem. Soc., vol. 124, pp. 7421-7428, (2002).
Kondratov, S.A., et al., "Nucelophilic substitution in the aromatic series. Lv. Reaction of o-nitrochlorobenzene with ammonia in the presence of copper compounds," Zhurnal Organidreskoi Khimii, vol. 51, No. 11, pp. 2387-2390, (1979).
Koppel, J., et al., "Optimal Treatment of Alzheimer's Disease Psychosis: Challenges and Solutions," Neuropsychiatric Disease and Treatment, vol. 10, pp. 2253-2262, (2014).
Kudla, et al., "Influence of G protein-biased agonists of μ-opioid receptor on addiction-related behaviors," *Pharmacol Rep.*, 73(4), pp. 1033-1051, (2021).
Kwong, F.Y., et al., "Mild and efficient copper-catalyzed amination of aryl bromides with primary alkylamines," Organic Letters, vol. 5, No. 6, pp. 793-796, (2003).

(56) References Cited

OTHER PUBLICATIONS

Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013).
Lebert, F., et al., "Trazodone in Fronto-Temporal Dementia", Research and Practice in Alzheimer's Disease, vol. 11, 356-360, (2006).
Lee, T., et al. "Novel, Highly Potent, Selective 5-HT2A/D2 Receptor Antagonists as Potential Atypical Antipsychotics," Bioorg. Med. Chem. Lett. vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Lieberman, J.A., et al., "ITI-007 for the Treatment of Schizophrenia: A 4-Week Randomized, Double-Blind, Controlled Trial," Biol. Psychiatry, vol. 79, No. 12, pp. 952-961, (2015).
Lin, Y-T., et al., "Dosage and Duration of Antipsychotic Treatment in Demented Outpatients with Agitation or Psychosis," Journal of the Formosan Medical Association, vol. 114, pp. 147-153, (2015).
Lipschitz, D.S., et al., "Childhood Posttraumatic Stress Disorder: A Review of Neurobiologic Sequelae", Psychiatric Annals Journal, vol. 28, Issue 8, p. 452-457, (1998).
Lopez, et al., "Psychiatric Symptoms Vary with the Severity of Dementia in Probably Alzheimer's Disease," J. Neuropsychiatry Clin. Neurosc., vol. 15, No. 3, pp. 346-353, (2003).
Louie, J., et al., "Palladium-Catalyzed Synthesis of Arylamines from Aryl Halides, Mechanistic Studies lead to Coupling in the Absence of Tin Reagents", Tetrahedron Letters, vol. 36, No. 21, p. 3609-3612, (1995).
Lounkine, E., et al., "Formal Concept Analysis for the Identification of Molecular Fragment Combinations Specific for Active and Highly Potent Compounds," J. Med. Chem., vol. 51, No. 17, pp. 5342-5348, (2008).
Madhusoodanan, S., et al., "Pharmacological Management of Behavioral Symptoms Associated with Dementia," World J. Psychiatr., vol. 4, No. 4, pp. 72-79, (2014).
March et al, Advanced Organic Chemistry; Reactions, Mechanisms and Structures, Fourth Edition, pp. 910-911 (1992).
Marcoux, J-F., et al., "A general copper-catalyzed synthesis of diaryl ethers," J. Am. Chem. Soc., vol. 119, pp. 10539-10540, (1997).
Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).
Mohamed, S., et al., "Pharmacotherapy of PTSD in the U.S. Department of Veterans Affairs: diagnostic- and symptom-guided drug selection", J. Clin. Psychiatry, vol. 69, pp. 959-965, (2008).
Morgan, C.A., et al., "Acoustic Startle in Individuals With Posttraumatic Stress Disorder", Psychiatric Annals Journal, vol. 28, Issue 8, p. 430-434, (1998).
Mulrooney, C., et al., "Recent developments in copper-catalyzed n-arylation with aryl halides," Essay—University of Pennsylvania (2004).
Murakami et al., "Fischer Indolization of Ethyl Pyruvate 2-[2-(Trifluoromethyl)phenyl]-phenylhydrazone and New Insight into the Mechanism of the Goldberg Reaction." Chem. Pharm. Bull., vol. 43, No. 8, p. 1281-1286, (1995).
Nagai, Y., et al., "Synthesis of 2,3,4,4a,5,9b-hexahydro-1H-pyrido[4,3-b] indole derivatives and their central nervous system activities." Journal of Medicinal Chemistry, vol. 22, No. 6, p. 677-683, (1979).
Newman, A.W., et al., "Solid-state analysis of the active pharmaceutical ingredient in drug products", Drug Discovery Today, vol. 8, No. 19, 898-903 (2003).
Noble, F., et al., "The Opiod Receptors as Targets for Drug Abuse Medication," British Journal of Pharmacology, vol. 172, pp. 3964-3979, (2015); DOI: 10.1111/bph.13190.
Perlis et al., "Clinical Features of Bipolar Depression Versus Major Depressive Disorder in Large Multicenter Trials", Am J Psychiatry, vol. 163, p. 225-231, (2006).

Pond, S.M. et al., "Stereospecific reduction of haloperidol in human tissues". Biochemical Pharmacology, vol. 44, No. 5, p. 867-871 (1992).
Press Release, "Intra-Cellular Therapies Announces Additional Results from Phase 1/11 Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=8 84325), accessed on May 31, 2016.
Pubchem, CID-22036753, p. 4, pp. 1-12 (2007).
Pubchem, CID-9953107, p. 3, pp. 1-9 (2006).
Rackova, L., et al., "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548, (2006).
Rainer, M.K., "Risperidone long-acting injection: a review of its long term safety and efficacy," Neuropsychiatric Disease and Treatment, vol. 4, No. 5, pp. 919-927 (2008).
Sadighi, J.P., et al., "A highly active palladium catalyst system for the arylation of anilines," Tetrahedron Letters, vol. 39, pp. 5327-5330, (1998).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Savjani, K., et al., "Drug Solubility: Importance and Enhancement Techniques", International Scholarly Research Network Pharmaceutics, vol. 2012, pp. 1-10, (2012).
Sigel, H., et al., "Tenary Complexes in Solution", Inorganic Chemistry, vol. 13, No. 2, p. 462-465 (1974).
Singhal, D., et al., "Drug polymorphism and dosage form design: a practical perspective," Advanced Drug Delivery Reviews, vol. 56, pp. 335-347 (2004).
Skoog, D., et al., "Principles of Instrumental Analysis, 4th Edition", p. 577 (1992).
Snyder, G.L., et al., "Functional profile of a novel modulator of serotonin, dopamine, and glutamate neurotransmission," Psychopharmacology, vol. 232, p. 605-621 (2015) Published online Aug. 2014, DOI 10.1007/s00213-014-3704-1.
Snyder, et al., Advances in Pharmacology (vol. 90), Chapter 11, pp. 254-276, (Zorn et al., Eds.) (Academic Press, 2021).
Southwick, S.M., et al., "Neuroendocrine Alterations in Posttraumatic Stress Disorder," Psychiatric Annals Journal, vol. 28, Issue 8, p. 436-442, (1998).
Sugahara, M., et al., "A Facile Copper-Catalyzed Ullman Condensation: N-Arylation of Heterocyclic Compounds Containing an—NHCO—Moiety", Chem. Pharm. Bull., vol. 45, No. 4, p. 719-721, (1997).
Sullivan, et al., "Exploring Opioid-Sparing Multimodal Analgesia Options in Trauma: A Nursing Perspective", *Journal of Trauma Nursing*, 23(6), pp. 361-375, (2016).
Suppes, et al., "Adjunctive lumateperone (ITI-007) in the treatment of bipolar depression: Results from a randomized placebo-controlled clinical trial", Bipolar Disorders, pp. 1-11, (2023).
Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).
Tariot, et al., "Memantine Treatment in Patients with Moderate to Severe Alzheimer Disease Already Receiving Donepezil: A Randomized Controlled Trail," JAMA, vol. 291, No. 3, pp. 317-324, (2004).
Titulaer, et al., "Lumateperone-mediated effects on prefrontal glutamatergic receptor-mediated neurotransmission: A dopamine D1 receptor dependent mechanism", *European Neuropsychopharmacology*, vol. 62, pp. 22-35, (2022).

(56) References Cited

OTHER PUBLICATIONS

Torralva, et al., "Fentanyl but not Morphine Interacts with Nonopioid Recombinant Human Neurotransmitter Receptors and Transporters," J Pharmacol Exp Ther., 374(3), pp. 376-391, (2020).
Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).
Vanover, et al., "Dopamine D2 receptor occupancy of lumateperone (ITI-007): a Positron Emission Tomography Study in patients with schizophrenia," Neuropsychopharmacology 44:598-605, (2019).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, K., et al., "ITI-007: A Novel Therapy for the Treatment of Schizophrenia and Related Psychoses," International Clinical Psychopharamcology, vol. 26, e56, 1 page, (2011).
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.
Wagaw, S., et al., "A palladium-catalyzed method for the preparation of indoles via the Fischer indole synthesis," Journal of the American Chemical Society, vol. 121, No. 44, p. 10251-10263, (1999).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules, D., et al., "Acetylcholinesterase Inhibitor and N-Methyl-D-Aspartic Acid Receptor Antagonist Use among Hospice Enrollees with a Primary Diagnosis of Dementia", Journal of Palliative Medicine, vol. 11, No. 5, pp. 738-745 (2008).
Wiese, M., "Dsc Detection of Polymorphism in Pharmaceutical Anhydrous Dexamethasone Acetate," TA Instruments, TA 302, pp. 1-4 (2002).
Wolfe, J.P., et al., "An improved catalyst system for aromatic carbon-nitrogen bond formation: The possible involvement of bis(phosphine) palladium complexes as key intermediates," J. Am. Chem. Soc., vol. 118, pp. 7215-7216, (1996).
Wolfe, J.P., et al., "Intramolecular palladium-catalyzed aryl amination and aryl amidation," Tetrahedron, vol. 52, No. 21, pp. 7525-7546, (1996).
Wolter, M., et al., "Synthesis of N-aryl hydrazides by copper-catalyzed coupling of hydrazides with aryl iodides," Organic Letters, vol. 3, No. 23, pp. 3803-3805, (2001).
Yamada, K., et al., "A mild copper-mediated intramolecular amination of aryl halides," Synlett, No. 2, pp. 231-234, (2002).
Yang, B.H., "The development of efficient protocols for the palladium-catalyzed cyclization reactions of secondary amides and carbamates," Organic Letters, vol. 1, No. 1, pp. 35-37, (1999).
Yudofsky, S., et al., "Propranolol in the Treatment of Rage and Violent Behavior in Patients with Chronic Brain Syndromes", Am. J. Psychiatry, vol. 138, p. 218-220, (1981).
Zhang, Z., et al., "Highly efficient copper-catalyzed N-arylation of alkylamines with aryl iodides using phosphoramidite as ligand", Catalysis Communications, vol. 6, p. 784-787, (2005).
Zhang, et al., "The in vivo effects of olanzapine and other antipsychotic agents on receptor occupancy and antagonism of dopamine D1, D2, D3, 5HT2A and muscarinic receptors", Psychopharmacology, vol. 141, pp. 267-278, (1999).
Davis, R. et al., "ITI-007 in the treatment of schizophrenia: from novel pharmacology to clinical outcomes," Expert Review of Neurotherapeutics, vol. 16, No. 6, pp. 601-614 (2016).
Davis, R. et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis, R. et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Makadia, H. et al., "Poly Lactic-co-Glycolic Acid (PLGA) as Biodegradable Controlled Drug Delivery Carrier," Polymers (Basel), vol. 3, No. 3, pp. 1377-1397, (2011).
Volcow, N. et al., "Opioid Abuse in Chronic Pain Misconceptions and Mitigation Strategies," The New England Journal of Medicine, vol. 374, No. 13, pp. 1253-1263, (2016).

\* cited by examiner

PHARMACEUTICAL COMPOSITIONS COMPRISING HETEROCYCLE FUSED GAMMA CARBOLINE PRODRUGS

CROSS-REFERENCE TO RELATED APPLICATIONS

This application is a continuation of U.S. application Ser. No. 17/813,473, filed on Jul. 19, 2022, which is a division of U.S. application Ser. No. 16/634,059, filed on Jan. 24, 2020, which is a U.S. National Stage application under 35 U.S.C. § 371 of International Application No. PCT/US2018/043102, filed on Jul. 20, 2018, which claims priority to and the benefit of U.S. Provisional Application Nos. 62/537,292, filed on Jul. 26, 2017, and 62/647,492, filed on Mar. 23, 2018; the contents of each of which are incorporated by reference in their entirety.

FIELD OF THE INVENTION

The invention relates to particular prodrugs of substituted heterocycle fused gamma-carbolines, in free, solid, pharmaceutically acceptable salt and/or substantially pure form as described herein, pharmaceutical compositions thereof, and methods of use in the treatment of diseases involving the 5-$HT_{2A}$ receptor, the serotonin transporter (SERT), pathways involving dopamine $D_1$ and/or $D_2$ receptor signaling systems, and/or the µ-opioid receptor, e.g., diseases or disorders such as anxiety, psychosis, schizophrenia, sleep disorders, sexual disorders, migraine, conditions associated with pain (including cephalic pain, neuropathic pain, and as an acute analgesic), fibromyalgia, chronic fatigue, social phobias, gastrointestinal disorders such as dysfunction of the gastrointestinal tract motility and obesity; depression and mood disorders, such as those associated with psychosis or Parkinson's disease; psychosis such as schizophrenia associated with depression; bipolar disorder; drug dependencies, such as opiate dependency and alcohol dependency, drug withdrawal symptoms; obsessive-compulsive disorder (OCD), obsessive-compulsive personality disorder (OCPD), and related disorders; and other psychiatric and neurological conditions, as well as to combinations with other agents. In some embodiments, the disease or disorders may include treatment-resistant depression, cocaine dependency, and/or amphetamine dependency, opioid use disorder and the symptoms of opioid withdrawal.

BACKGROUND OF THE INVENTION

Substituted heterocycle fused gamma-carbolines are known to be agonists or antagonists of 5-$HT_2$ receptors, particularly 5-$HT_{2A}$ and 5-$HT_{2C}$ receptors, in treating central nervous system disorders. These compounds have been disclosed in U.S. Pat. Nos. 6,548,493; 7,238,690; 6,552,017; 6,713,471; 7,183,282; RE39,680, and RE39,679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. PCT/US08/03340 (WO 2008/112280), and its U.S. equivalent US 2010/113781 and U.S. application Ser. No. 10/786,935 (published as US 2004/209864) also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, WO/2009/145900 (and its equivalent US 2011/071080) discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects associated with high occupancy of the dopamine $D_2$ pathways or side effects of other pathways (e.g., $GABA_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. WO 2009/114181 (and its equivalent US 2011/112105) also discloses of methods of preparing toluenesulfonic acid addition salt crystals of these substituted heterocycle fused gamma-carbolines.

In addition, recent evidence shows that the aforementioned substituted fused heterocycle gamma carbolines may operate, in part, through NMDA receptor antagonism via mTOR1 signaling, in a manner similar to that of ketamine Ketamine is a selective NMDA receptor antagonist. Ketamine acts through a system that is unrelated to the common psychogenic monoamines (serotonin, norepinephrine and dopamine), and this is a major reason for its much more rapid effects. Ketamine directly antagonizes extrasynaptic glutamatergic NMDA receptors, which also indirectly results in activation of AMPA-type glutamate receptors. The downstream effects involve the brain-derived neurotrophic factor (BDNF) and mTORC1 kinase pathways. Similar to ketamine, recent evidence suggests that compounds related to those of the present disclosure enhance both NMDA and AMPA-induced currents in rat medial prefrontal cortex pyramidal neurons via activation of D1 receptors, and that this is associated with increased mTORC1 signaling.

The related publications WO 2017/132408 and US 2017/319580 disclose novel oxo-metabolites of the compounds disclosed in the above-mentioned publications. These new oxo-metabolites retain much of the unique pharmacologic activity of the parent compounds, including serotonin receptor inhibition, SERT inhibition, and dopamine receptor modulation. However, these oxo-metabolites were found to unexpectedly also show significant activity at mu-opiate receptors.

Obsessive-compulsive disorder (OCD) and related disorders, have become highly prevalent and are difficult to treat. OCD is estimated to affect about 2.3% of people at some point in their lives, and during a given year, it is estimated than 1.2% of people worldwide suffer from the disorder. Half of people who suffer from OCD begin to show symptoms before the age of 20, which can seriously affect their ability to obtain an adequate and effective education. Without effective treatment, however, the disease can last for decades. The mainstay of pharmacologic OCD treatment is with selective serotonin reuptake inhibitors (SSRIs). A second line of therapy is with antipsychotic agents, such as clomipramine, risperidone, quetiapine and olanzapine. A significant number of patients either do not respond to these agents, or cannot handle the side effects caused by these agents. More recently, it has been reported that the opioid analgesic tramadol may be effective in treating OCD. Opiates operate by an entirely different pathway from traditional OCD treatment agents, so they offer the possibility of treatment for people who cannot take the traditional serotonergic agents or for whom these agents are ineffective. However, strong opiate agents can be addictive, and their use may be contraindicated in some patients. There thus remains an urgent need for new treatments for pain, OCD and other disorders.

Drug dependency disorders, such as opiate use disorder (OUD), are another group of disorders which are difficult to successfully treat. Opioid overdoses claim approximately 100 lives in the United States every day, and the opioid epidemic continues to grow in the United States. Methadone, buprenorphine, and naltrexone are the most frequently used treatments for OUD. Methadone is a mu-opioid receptor (MOP) agonist, buprenorphine is an MOP partial agonist, and naltrexone is an MOP antagonist. Each of these agents has had limited success, and long-term adherence to prescribed therapies for OUD remains low. In addition, these treatments often exacerbate common co-morbidities associated with OUD, such as mood and anxiety disorders, which further increases the risk of remission. Abrupt opioid abuse withdrawal (i.e., going "cold turkey") is also associated with severe side effects, including dysphoria, depression and anxiety, and the common treatment agents do not address these problems, and may make them worse. There is thus an urgent need for improved OUD treatments.

SUMMARY OF THE INVENTION

Compounds of Formula A and B, shown below, are potent serotonin 5-HT$_{2A}$ receptor antagonists and mu-opiate receptor partial agonists or biased agonists. These compounds also interact with dopamine receptors, particular the dopamine D1 receptors.

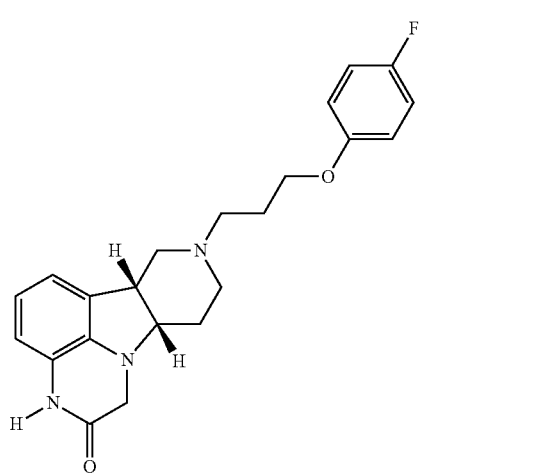

Formula A

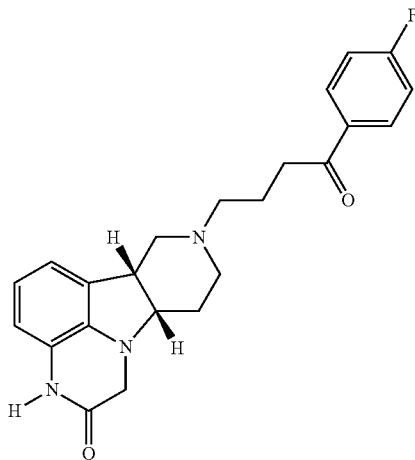

Formula B

It is also believed that the Compounds of Formula A and/or B, via their D1 receptor activity, may also enhance NMDA and AMPA mediated signaling through the mTOR pathway. The Compounds of Formula A and B and their analogs are useful for the treatment or prophylaxis of central nervous system disorders, but there is a need in the art for prodrugs of the Compounds of Formula A and B that when administered to a patient can provide for improved therapeutic concentrations or improved pharmacokinetic distribution or dynamics of these compounds. The present disclosure fills this need by providing Compounds of Formula I and II, et seq., which are prodrugs of the Compounds of Formula A and B, and their analogs. Due to their useful metabolic and pharmacokinetic profile, the Compounds of the present disclosure are particularly suited for formulation as long-acting or extended-release compositions that when administered to a patient can provide for improved therapeutic amounts concentrations of the compounds A and B and their analogs over an extended period of time.

In a first aspect, the present disclosure relates to a compound (Compound I) of Formula I:

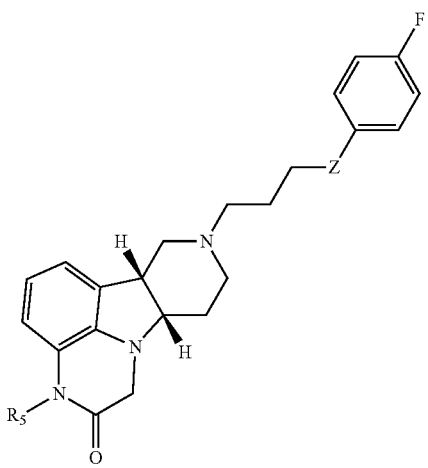

Formula I wherein:
R$^5$ is —C(O)—O—C(R$^a$)(R$^b$)(R$^c$), —C(O)—O—CH$_2$—O—C(R$^a$)(R$^b$)(R$^c$) or —C(R$^6$)(R$^7$)—O—C(O)—R$^8$;

Z is O, or —C(O)—;

$R^8$ is —C($R^a$)($R^b$)($R^c$), —O—C($R^a$)($R^b$)($R^c$), or —N($R^d$)($R^e$);

$R^a$, $R^b$ and $R^c$ are each independently selected from H and $C_{1-24}$alkyl;

$R^d$ and $R^e$ are each independently selected from H and $C_{1-24}$alkyl;

$R^6$ and $R^7$ are each independently selected from H, $C_{1-6}$alkyl, carboxy and $C_{1-6}$alkoxycarbonyl;

in free or salt form (e.g., pharmaceutically acceptable salt form), for example in an isolated or purified free or salt form (e.g., pharmaceutically acceptable salt form).

The present disclosure provides additional exemplary embodiments of the Compound of Formula I, in free or salt form (e.g., pharmaceutically acceptable salt form), for example in an isolated or purified free or salt form (e.g., pharmaceutically acceptable salt form), including:

1.1 Compound I, wherein Z is O;

1.2 Compound I, wherein Z is —C(O);

1.3 Compound I, 1.1, or 1.2, wherein $R^5$ is —C(O)—O—C($R^a$)($R^b$)($R^c$);

1.4 Compound 1.3, wherein $R^a$ is H and $R^b$ and $R^c$ are each independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.5 Compound 1.3, wherein $R^a$ and $R^b$ are H and $R^c$ is $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.6 Compound 1.3, wherein $R^a$, $R^b$ and $R^c$ are each independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.7 Compound 1.3, wherein $R^a$, $R^b$ and $R^c$ are each H;

1.8 Compound 1.3, wherein Z is O and $R^a$ and $R^b$ are H and $R^c$ is $C_{10-14}$alkyl (e.g., $R^c$ is $CH_3(CH_2)_{10}$ or $CH_3(CH_2)_{14}$);

1.9 Compound I, 1.1, or 1.2, wherein $R^5$ is —C(O)—O—CH$_2$—O—C($R^a$)($R^b$)($R^c$);

1.10 Compound 1.9, wherein $R^a$ is H and $R^b$ and $R^c$ are each independently selected from $C_{1-24}$alkyl, e.g., $C_{1-20}$alkyl, $CH_{5-20}$alkyl, $CH_{9-18}$alkyl, $CH_{10-16}$alkyl, or $C_{11}$alkyl, $C_{12}$alkyl, $C_{13}$alkyl, $C_{14}$alkyl, $C_{15}$alkyl or $C_{16}$alkyl;

1.11 Compound 1.9, wherein $R^a$ and $R^b$ are H and $R^c$ is $C_{1-24}$alkyl, e.g., $C_{1-20}$alkyl, $C_{5-20}$alkyl, $CH_{9-18}$alkyl, $CH_{10-16}$alkyl, or $C_{11}$alkyl, $C_{12}$alkyl, $C_{13}$alkyl, $C_{14}$alkyl, $C_{15}$alkyl or $C_{16}$alkyl;

1.12 Compound 1.9, wherein $R^a$, $R^b$ and $R^c$ are each independently selected from $C_{1-24}$alkyl, e.g., $C_{1-20}$alkyl, $CH_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.13 Compound 1.9, wherein $R^a$, $R^b$ and $R^c$ are each H;

1.14 Compound I, 1.1, or 1.2, wherein $R^5$ is —C($R^6$)($R^7$)—O—C(O)—$R^8$, and $R^8$ is —C($R^a$)($R^b$)($R^c$);

1.15 Compound I, 1.1, or 1.2, wherein $R^5$ is —C($R^6$)($R^7$)—O—C(O)—$R^8$, and $R^8$ is —O—C($R^a$)($R^b$)($R^c$);

1.16 Compound 1.14 or 1.15, wherein $R^a$ is H and $R^b$ and $R^c$ are each independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.17 Compound 1.14 or 1.15, wherein $R^a$ and $R^b$ are H and $R^c$ is $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.18 Compound 1.14 or 1.15, wherein $R^a$, $R^b$ and $R^c$ are each independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.19 Compound 1.14 or 1.15, wherein $R^a$, $R^b$ and $R^c$ are each H;

1.20 Compound 1.14, wherein Z is O and $R^6$ is H, and $R^7$ is $C_{1-3}$alkyl (e.g., $R^7$ is methyl or isopropyl), and $R^8$ is $C_{10-14}$alkyl (e.g., $R^8$ is $CH_3(CH_2)_{10}$ or $CH_3(CH_2)_{14}$);

1.21 Compound I, 1.1, or 1.2, wherein $R^5$ is —C($R^6$)($R^7$)—O—C(O)—$R^8$, and $R^8$ is —N($R^d$)($R^e$);

1.22 Compound 1.21, wherein $R^d$ is H and $R^e$ is independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.23 Compound 1.21, wherein $R^d$ and $R^4$ are each independently selected from $C_{1-24}$alkyl, e.g., $C_{1-20}$alkyl, $C_{5-20}$alkyl, $C_{9-18}$alkyl, $C_{10-16}$alkyl, or $C_{11}$alkyl, $C_{12}$alkyl, $C_{13}$alkyl, $C_{14}$alkyl, $C_{15}$alkyl or $C_{16}$alkyl;

1.24 Compound 1.21, wherein $R^d$ and $R^4$ are each H;

1.25 Any of Compounds 1.14-1.24, wherein $R^6$ is H and $R^7$ is H;

1.26 Any of Compounds 1.14-1.24, wherein $R^6$ is $C_{1-6}$alkyl and $R^7$ is $C_{1-6}$alkyl;

1.27 Any of Compounds 1.14-1.24, wherein $R^6$ is H and $R^7$ is $C_{1-6}$alkyl;

1.28 Any of Compounds 1.14-1.24, wherein $R^6$ is H and $R^7$ is carboxy;

1.29 Any of Compounds 1.14-1.24, wherein $R^6$ is H and $R^7$ is $C_{1-6}$alkoxycarbonyl, e.g., ethoxycarbonyl or methoxycarbonyl;

1.30 Compound I, or any of 1.1-1.29, in free form;

1.31 Compound I, or any of 1.1-1.29 in salt form, e.g., pharmaceutically acceptable salt form;

1.32 Compound I, or any of 1.1-1.31, in substantially pure diastereomeric form (i.e., substantially free from other diastereomers);

1.33 Compound I or any of 1.1-1.31, having a diastereomeric excess of greater than 70%, preferably greater than 80%, more preferably greater than 90% and most preferably greater than 95%.

1.34 Compound I or any of 1.1-1.33 in solid form.

in free or salt form (e.g., pharmaceutically acceptable salt form), for example in an isolated or purified free or salt form (e.g., pharmaceutically acceptable salt form).

In a second aspect, the present disclosure relates to a compound (Compound II) of Formula II:

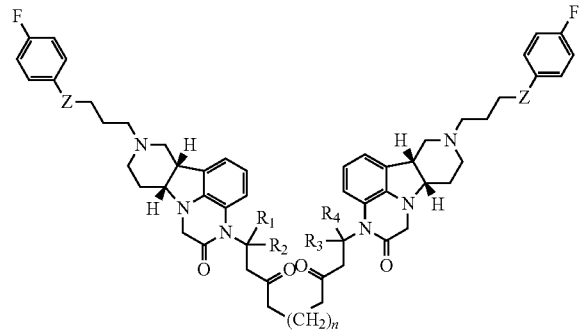

Formula II wherein:

Z is O, or —C(O)—;

$R^1$, $R^2$, $R^3$ and $R^4$ are each independently selected from H and $C_{1-6}$alkyl;

n is an integer from 1 to 23;

in free or salt form (e.g., pharmaceutically acceptable salt form), for example in an isolated or purified free or salt form (e.g., pharmaceutically acceptable salt form).

The present disclosure provides additional exemplary embodiments of the Compound of Formula II, in free or salt form (e.g., pharmaceutically acceptable salt form), for example in an isolated or purified free or salt form (e.g., pharmaceutically acceptable salt form), including:

2.1 Compound II, wherein Z is O;

2.2 Compound II, wherein Z is —C(O);

2.3 Compound II, 2.1, or 2.2, wherein $R^1$ and $R^3$ are H and $R^2$ and $R^4$ are each independently selected from $C_{1-6}$alkyl, e.g., $C_{1-4}$alkyl, $C_{1-3}$alkyl, or $C_{1-2}$alkyl;

2.4 Compound II, 2.1, or 2.2, wherein $R^1$ and $R^2$ are H and $R^3$ and $R^4$ are each independently selected from $C_{1-6}$alkyl, e.g., $C_{1-4}$alkyl, $C_{1-3}$alkyl, or $C_{1-2}$alkyl;

2.5 Compound II, 2.1, or 2.2, wherein $R^1$, $R^2$, $R^3$ and $R^4$ are each independently selected from $C_{1-6}$alkyl, e.g., $C_{1-4}$alkyl, $C_{1-3}$alkyl, or $C_{1-2}$alkyl;

2.6 Compound II, 2.1, or 2.2, wherein $R^1$, $R^2$, $R^3$ and $R^4$ are each H;

2.7 Compound II or any of compounds 2.1-2.6, wherein n is an integer from 1-21, e.g., from 3-21 or from 3-15 or from 5-15 or from 7-13 or from 7-11;

2.8 Compound II, or any of 2.1-2.7, in free form;

2.9 Compound II, or any of 2.1-2.7 in salt form, e.g., pharmaceutically acceptable salt form;

2.10 Compound II, or any of 2.1-2.7 in solid form.

in free or salt form (e.g., pharmaceutically acceptable salt form), for example in an isolated or purified free or salt form (e.g., pharmaceutically acceptable salt form).

In a third aspect, the present disclosure provides each of the foregoing Compound I or 1.1-1.34, Compound II or 2.1-2.10, (hereinafter collectively "Compounds of Formulas I-II et seq." or "compounds of the disclosure") in pharmaceutically acceptable salt form (e.g., pharmaceutically acceptable salt form). The present disclosure provides additional exemplary embodiments of the Compounds of Formulas I-II et seq., including:

5.1 Compounds of Formulas I-II et seq., wherein the salt is an acid addition salt selected from hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;

5.2 Compounds of Formulas I-II et seq., wherein the salt is fumaric acid addition salt;

5.3 Compounds of Formulas I-II et seq., wherein the salt is phosphoric acid addition salt;

5.4 Compounds of Formulas I-II et seq., wherein the salt is a toluenesulfonic acid addition salt;

5.5 Any of 5.1-5.4 wherein the salt is in solid form.

In a fourth aspect, the present disclosure provides a pharmaceutical composition (Pharmaceutical Composition 6) comprising a compound according to any one of Compound I or 1.1-1.34, Compound II or 2.1-2.10, (collectively, Compounds of Formulas I-II et seq. or compounds of the disclosure), e.g., in admixture with a pharmaceutically acceptable diluent or carrier. The present disclosure provides additional exemplary embodiments of Pharmaceutical Composition 6, including:

6.1 Pharmaceutical Composition 6, comprising Compound I or any of 1.1-1.34;

6.2 Pharmaceutical Composition 6, comprising Compound II or any of 2.1-2.10;

6.3 Pharmaceutical Composition 6 or any of 6.1-6.2, wherein the Compound of Formula I-II et seq. is in solid form;

6.4 Pharmaceutical Composition 6 or any of 6.1-6.3, wherein the Compound of Formulas I-II et seq. is in pharmaceutically acceptable salt form (e.g., pharmaceutically acceptable salt form) as described in Compounds 5.1-5.5;

6.5 Pharmaceutical Composition 6 or any of 6.1-6.4, wherein the Compound of Formulas I-II et seq. is in admixture with a pharmaceutically acceptable diluent or carrier.

In a further embodiment, the Pharmaceutical Compositions of the present disclosure, are for a sustained or delayed release, e.g., depot, formulation. In one embodiment, the depot formulation (Depot Formulation 6.6) is the Pharmaceutical Composition of any of 6.1-6.5, preferably in free or pharmaceutically acceptable salt form, and preferably in admixture with a pharmaceutically acceptable diluent or carrier, e.g., providing sustained or delayed release as an injectable depot.

In a particular embodiment, the Depot Formulation 6.6 comprises a compound according to any one of Compound I or 1.1-1.34, or Compound II or 2.1-2.10, in free base or pharmaceutically acceptable salt form, optionally in crystal form, wherein the compound has been milled to, or the compound crystallized to, microparticle or nanoparticle size, e.g., particles or crystals having a volume-based particle size (e.g., diameter or Dv50) of 0.5 to 100 microns, for example, for example, 5-30 microns, 10-20 microns, 20-100 microns, 20-50 microns or 30-50 microns. Such particles or crystals may be combined with a suitable pharmaceutically acceptable diluent or carrier, for example water, to form a depot formulation for injection. For example, the depot formulation may be formulated for intramuscular or subcutaneous injection with a dosage of drug suitable for 4 to 6 weeks of treatment. In some embodiments, the particles or crystals have a surface area of 0.1 to 5 $m^2/g$, for example, 0.5 to 3.3 $m^2/g$ or from 0.8 to 1.2 $m^2/g$.

In another embodiment, the present disclosure provides Pharmaceutical Composition 6.7, which is Pharmaceutical Composition 6 or any of 6.1-6.6, wherein the Compound of Formulas I-II et seq. is in a polymeric matrix. In one embodiment, the Compound of the present disclosure is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly (glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

The (Pharmaceutical) Compositions 6 and 6.1-6.7 are particularly useful for sustained or delayed release, wherein the Compound of the present disclosure is released upon degradation of the polymeric matrix. These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Compositions of the present disclosure, for example the depot composition of the present disclosure, e.g., Pharmaceutical Composition 6.6 or 6.7, is formulated for administration by injection.

In a fifth aspect, the present disclosure provides the Compounds of Formulas I-II et seq. as hereinbefore described, in an osmotic controlled release oral delivery system (OROS), which is described in WO 2000/35419 (US 2001/0036472) and EP 1 539 115 (U.S. Pub. No. 2009/0202631), the contents of each of which applications are incorporated by reference in their entirety. Therefore in one embodiment of the seventh aspect, the present disclosure provides a pharmaceutical composition or device comprising (a) a gelatin capsule containing a Compound of any of Formulae I-II et seq. in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall (Pharmaceutical Composition P.1).

In another embodiment, the invention provides a pharmaceutical composition comprising a gelatin capsule containing a liquid, the Compound of Formulas I-II et seq. in free or pharmaceutically acceptable salt form or a Pharmaceutical Composition of the Invention, e.g., any of Pharmaceutical Composition 6 or 6.1-6.7, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall (Pharmaceutical Composition P.2).

In still another embodiment of the seventh aspect, the invention provides a composition comprising a gelatin capsule containing a liquid, the Compound of Formulas I-II et seq. in free or pharmaceutically acceptable salt form or a Pharmaceutical Composition of the Invention, e.g., any of Pharmaceutical Composition 6 or 6.1-6.7, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice (Pharmaceutical Composition P.3).

In still another embodiment of the seventh aspect, the invention provides a composition comprising a gelatin capsule containing a liquid, the Compound of Formulas I-II et seq. in free or pharmaceutically acceptable salt form or a Pharmaceutical Composition of the Invention, e.g., any of Pharmaceutical Composition 6 or 6.1-6.7, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use (Pharmaceutical Composition P.4). The expandable layer may be formed in one or more discrete sections, such as for example, two sections located on opposing sides or ends of the gelatin capsule.

In a particular embodiment of the seventh aspect, the Compound of the present disclosure in the Osmotic-controlled Release Oral Delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral Delivery System composition including characteristics of the gelatin capsule, barrier layer, an expandable layer, a semi-permeable layer; and orifice may be found in WO 2000/35419 and US 2001/0036472, the contents of which are incorporated by reference in their entirety.

Other Osmotic-controlled Release Oral Delivery System for the Compound of Formulas I-II et seq. or the Pharmaceutical Composition of the present disclosure may be found in EP 1 539 115 (U.S. Pub. No. 2009/0202631), the contents of which are incorporated by reference in their entirety. Therefore, in another embodiment of the seventh aspect, the invention provides a composition or device comprising (a) two or more layers, said two or more layers comprising a first layer and a second layer, said first layer comprises the Compound of Formulas I-II et seq., in free or pharmaceutically acceptable salt form, or a Pharmaceutical Composition as herein before described said second layer comprises a polymer; (b) an outer wall surrounding said two or more layers; and (c) an orifice in said outer wall (Pharmaceutical Composition P.5).

Pharmaceutical Composition P.5 preferably utilizes a semi-permeable membrane surrounding a three-layer-core: in these embodiments, the first layer is referred to as a first drug layer and contains low amounts of drug (e.g., the Compound of Formulas I-II et seq.) and an osmotic agent such as salt, the middle layer referred to as the second drug layer contains higher amounts of drug, excipients and no salt; and the third layer referred to as the push layer contains osmotic agents and no drug (Pharmaceutical Composition P.6). At least one orifice is drilled through the membrane on the first drug layer end of the capsule-shaped tablet.

Pharmaceutical Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof (Pharmaceutical Composition P.7). Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers.

In a particular embodiment, the invention provides Pharmaceutical Composition P.7 wherein the first drug layer comprising salt and the second drug layer containing no salt. Pharmaceutical Composition P.5-P.7 may optionally comprise a flow-promoting layer between the membrane and the drug layers.

Pharmaceutical Compositions P.1-P.7 will generally be referred to as Osmotic-controlled Release Oral Delivery System Composition.

In a sixth aspect, the invention provides a method (Method 1) for the treatment or prophylaxis of a central nervous system disorder, comprising administering to a patient in need thereof a Compound of Formulas I-II et seq. or a Pharmaceutical Composition 6 or 6.1-6.7 or P.1-P.7, for example Method 1 wherein the compound or composition administered is:

1.1 Compound I or any of 1.1-1.34, in free or pharmaceutically acceptable salt form;
1.2 Compound II or any of 2.1-2.10, in free or pharmaceutically acceptable salt form;
1.3 The Compounds of Embodiment 5 or any of 5.1-5.5;
1.4 a Pharmaceutical Composition as described by any of Pharmaceutical Compositions 6 and 6.1-6.7;
1.5 Depot Composition as described in Depot Composition 6.6 or 6.7;
1.6 Pharmaceutical Composition P.1-P.7;
1.7 Osmotic-controlled Release Oral Delivery System Composition as hereinbefore described;

In a further embodiment of the sixth aspect, the present disclosure provides Method 1 or any of Methods 1.1-1.7, wherein the method is further as described as follows:

1.8 Method 1 or any of Methods 1.1-1.7, wherein the central nervous system disorder is a disorder selected from a group consisting of obesity, anxiety (including general anxiety, social anxiety, and panic disorders), depression (for example refractory depression and MDD), psychosis (including psychosis associated with dementia, such as hallucinations in advanced Parkinson's disease or paranoid delusions), schizophrenia, sleep disorders (particularly sleep disorders associated with schizophrenia and other psychiatric and neurological diseases), sexual disorders, migraine, pain and conditions associated with pain, including cephalic pain, idiopathic pain, chronic pain (such as moderate to moderately severe chronic pain, for example in patients requiring 24 hour extend treatment for other ailments), neuropathic pain, dental pain, fibromyalgia, chronic fatigue, agoraphobia, social phobias, agitation in dementia (e.g., agitation in Alzheimer's disease), agitation in autism and related autistic disorders, gastrointestinal disorders such as dysfunction of the gastrointestinal tract motility, and dementia, for example dementia of Alzheimer's disease or of Parkinson's disease; mood disorders; drug dependencies, for example, opiate dependency and/or alcohol dependency, and withdrawal from drug or alcohol dependency (e.g., opiate dependency); opiate overdose; co-morbidities associated with drug dependencies, such as depression, anxiety and psychosis; binge eating disorder; and obsessive-compulsive disorder (OCD), obsessive-compulsive personality disorder (OCPD) and related disorders; or opiate use disorder (OUD);

1.9 Method 1 or any of Methods 1.1-1.8, wherein the central nervous system disorder is a disorder involving serotonin 5-$HT_{2A}$, dopamine D1 and/or D2 receptor system and/or serotonin reuptake transporter (SERT) pathways as similarly described in WO/2009/145900 and US 2011/071080, the contents of which are herein incorporated by reference in their entirety;

1.10 Method 1 or any of Methods 1.1-1.9, wherein the central nervous system disorder is a disorder involving the μ-opioid receptor;

1.11 Method 1 or any of Methods 1.1-1.10, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis and/or drug dependencies, e.g., schizophrenia or Parkinson's disease; (4) sleep disorders associated with psychosis, e.g., schizophrenia or Parkinson's disease; and (5) substance addiction, substance use disorders and/or substance-induced disorders, optionally wherein the patient suffers from residual symptoms of anxiety or anxiety disorder; and optionally wherein the depression is treatment-resistant depression;

1.12 Method 1 or any of Methods 1.1-1.11, wherein the central nervous system disorder is psychosis, e.g., schizophrenia and said patient is a patient suffering from depression;

1.13 Method 1 or any of Methods 1.1-1.12, wherein said patient is unable to tolerate the side effects of conventional antipsychotic drugs, e.g., chlorpromazine, haloperidol, droperidol, fluphenazine, loxapine, mesoridazine molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone and ziprasidone;

1.14 Method 1 or any of Methods 1.1-1.13, wherein said patient is unable to tolerate the side effects of non-narcotic analgesics and/or opiate and opioid drugs, or wherein the use of opiate drugs are contraindicated in said patient, for example, due to prior substance abuse or a high potential for substance abuse, such as opiate and opioid drugs including, e.g., morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof.

1.15 Method 1 or any of Methods 1.1-1.14, wherein said patient is unable to tolerate the side effects of conventional antipsychotic drugs, e.g., haloperidol, brexpiprazole, cariprazine, asenapine, lurasidone, aripiprazole, clozapine, olanzapine, quetiapine, risperidone, and ziprasidone;

1.16 Method 1 or any of Methods 1.1-1.15, wherein said disorder is depression and said patient is a patient suffering from psychosis, e.g., schizophrenia, or Parkinson's disease;

1.17 Method 1 or any of Methods 1.1-1.15, wherein said disorder is sleep disorder and said patient is suffering from depression;

1.18 Method 1 or any of Methods 1.1-1.15, wherein said one or more disorders is sleep disorder and said patient is suffering from psychosis, e.g., schizophrenia;

1.19 Method 1 or any of Methods 1.1-1.15, wherein said one or more disorders is sleep disorder and said patient is suffering from Parkinson's disease;

1.20 Method 1 or any of Methods 1.1-1.15, wherein said one or more disorders is sleep disorder and said patient is suffering from depression and psychosis, e.g., schizophrenia, or Parkinson's disease.

1.21 Method 1 or any of 1.1-1.20, wherein said patient is suffering from a drug dependency disorder, optionally in conjunction with any preceding disorders, for example, wherein said patient suffers from opiate dependency, cocaine dependency, amphetamine dependency, and/or alcohol dependency, or from withdrawal from drug or alcohol dependency (e.g. opiate, cocaine, or amphetamine dependency), and optionally wherein the patient suffers from a co-morbidity, such as anxiety, depression or psychosis, or residual symptoms of anxiety or anxiety disorder and/or altered mood (e.g., depression); further optionally wherein the patient suffers from an opiate overdose;

1.22 Any of the foregoing methods, wherein the effective amount is 1 mg-1000 mg, for example 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.23 Any of the foregoing methods, wherein the effective amount is 1 mg-100 mg per day, for example 2.5 mg-50 mg per day;

1.24 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

1.25 Any of the foregoing methods wherein the patient suffers from Parkinson's disease.

Substance-use disorders and substance-induced disorders are the two categories of substance-related disorders defined by the Fifth Edition of the DSM (the Diagnostic and Statistical Manual of Mental Disorders, DSM-V). A substance-use disorder is a pattern of symptoms resulting from use of a substance which the individual continues to take, despite experiencing problems as a result. A substance-induced disorder is a disorder induced by use if the substance. Substance-induced disorders include intoxication, withdrawal, substance induced mental disorders, including substance induced psychosis, substance induced bipolar and related disorders, substance induced depressive disorders, substance induced anxiety disorders, substance induced obsessive-compulsive and related disorders, substance induced sleep disorders, substance induced sexual dysfunctions, substance induced delirium and substance induced neurocognitive disorders.

The DSM-V includes criteria for classifying a substance use disorder as mild, moderate or severe. In some embodiments of the methods disclosed herein, the substance use disorder is selected from a mild substance use disorder, a moderate substance use disorder or a severe substance use disorder. In some embodiments, the substance use disorder is a mild substance use disorder. In some embodiments, the substance use disorder is a moderate substance use disorder. In some embodiments, the substance use disorder is a severe substance use disorder.

Anxiety and depression are highly prevalent co-morbid disorders in patients undergoing treatment of substance use or substance abuse. A common treatment for substance abuse disorder is the combination of the partial opioid agonist buprenorphine with the opioid antagonist naloxone, but neither of these drugs has any significant effect on anxiety or depression, thus leading to the common result that a third drug, such as a benzodiazepine-class anxiolytic agent or an SSRI anti-depressant, must also be prescribed. This makes treatment regimens and patient compliance more difficult. In contrast, the Compounds of the present disclosure provide opiate antagonism along with serotonin antagonism and dopamine modulation. This may result in significant enhancement of treatment of patients with substance use or abuse disorder concomitant with anxiety and/or depression.

The compounds of the present disclosure may have anxiolytic properties ameliorating the need for treatment of a patient with an anxiolytic agent where said patients suffers from co-morbid anxiety. Thus, in some embodiments, the present disclosure provides a method according to Method 1, or any of Methods 1.1-1.25, wherein the central nervous system disorder is a substance addiction, substance use disorders and/or substance-induced disorders, or a substance abuse disorder, for example, in a patient suffering from symptoms of anxiety or who is diagnosed with anxiety as a co-morbid disorder, or as a residual disorder, wherein the method does not comprise the further administration of an anxiolytic agent, such as a benzodiazepine. Benzodiazepines are GABA-modulating compounds, including those discussed with reference to Method 3.1 and 3.2 below.

In another embodiment of the sixth aspect, the present disclosure provides Method 1 or any of Methods 1.1-1.7, wherein the method is further as described as follows:

1.26 Method 1 or any of Methods 1.1-1.25, wherein the central nervous system disorder is a disorder selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD), impulse control disorder, and related disorders, and combination thereof.

1.27 Method 1 or any one Method 1.1-1.25, wherein the central nervous system disorder is selected from obsessive-compulsive disorder (OCD), obsessive-compulsive personality disorder (OCPD), social anxiety disorder, panic disorder, agoraphobia, compulsive gambling disorder, compulsive eating disorder, body dysmorphic disorder and impulse control disorder.

1.28 Method 1 or any one of Method 1.1-1.25, wherein the central nervous system disorder is obsessive-compulsive disorder (OCD) or obsessive-compulsive personality disorder (OCPD).

1.29 Any foregoing method, wherein said patient is not responsive to or cannot tolerate the side effects from, treatment with selective serotonin reuptake inhibitors (SSRIs), such as citalopram, escitalopram, fluoxetine, fluvoxamine, paroxetine, and sertraline.

1.30 Any foregoing method, wherein said patient is not responsive to or cannot tolerate the side effects from, treatment with serotonin-norepinephrine reuptake inhibitors (SNRIs), such as venlafaxine, sibutramine, duloxetine, atomoxetine, desvenlafaxine, milnacipran, and levomilnacipran.

1.31 Any foregoing method, wherein said patient is not responsive to or cannot tolerate the side effects from, treatment with antipsychotic agents, such as clomipramine, risperidone, quetiapine and olanzapine.

1.32 Method 1 or any of Method 1.1-1.25, wherein the central nervous system disorder is a pain disorder, e.g., a condition associated with pain, such as cephalic pain, idiopathic pain, neuropathic pain, chronic pain (e.g., moderate to moderately severe chronic pain, for example, in patients requiring 24-hour extended treatment for other ailments), fibromyalgia, dental pain, traumatic pain, or chronic fatigue.

1.33 Any foregoing method, wherein the patient is not responsive to or cannot tolerate the side effects of non-narcotic analgesics and/or opiate and opioid drugs, or wherein the use of opiate drugs are contraindicated in said patient, for example, due to prior substance abuse or a high potential for substance abuse, such as opiate and opioid drugs including, e.g., morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof;

1.34 Method I or any of Methods 1.1-1.33, wherein the central nervous system disease or disorder is a drug dependency (for example, opiate dependency (i.e., opioid use disorder), cocaine dependency, amphetamine dependency, and/or alcohol dependency), or withdrawal from drug or alcohol dependency (e.g., opiate, cocaine, or amphetamine dependency), and wherein the patient also suffers from a co-morbidity, such as anxiety, depression or psychosis; optionally wherein the patient also suffers from an opiate overdose;

1.35 Any of the foregoing methods, wherein the effective amount is 1 mg-1000 mg, preferably 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.36 Any of the foregoing methods, wherein the effective amount is 1 mg-100 mg per day, preferably 2.5 mg-50 mg per day.

In still another embodiment, the present disclosure provides any of the Methods 1 or 1.1-1.36 as hereinbefore described wherein the disorder is schizophrenia or sleep disorder. In some embodiments, said schizophrenia is associated with depression.

In still another embodiment, the present disclosure provides any of Methods 1.1-1.36, wherein the Depot Composition of the Invention (e.g., Depot Composition of any of formulae 6.6-6.7), or (Pharmaceutical) Composition 6 or 6.1-6.7, or Pharmaceutical Composition P.1-P.7, is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In still another embodiment, the invention provides any Method 1 or 1.1-1.36 as hereinbefore described, wherein the Depot Composition of the present disclosure is administered for controlled- and/or sustained-release of the Compounds of the Invention over a period of time.

In another embodiment of the sixth aspect, the invention provides Method 1, or any of Methods 1.1-1.36, e.g., any method of treating pain, wherein the patient suffers from a gastrointestinal disorder and/or a pulmonary disorder. Traditional opioid analgesics suffer from two dominant side effects: gastrointestinal disturbances (including nausea, vomiting and constipation) and respiratory depression. 90 to 95% of patients taking opioids for long-term pain treatment develop serious constipation, requiring the long-term use of laxatives and/or enemas. The stronger opioids such as morphine, oxycodone and hydromorphone produce more severe constipation than other opioids. Respiratory depression is the most serious adverse effect of opioid treatment as it creates a risk of death, especially when patients combine (intentionally or inadvertently) prescribed opioid analgesics with other licit or illicit respiratory depressants (including alcohol). Patients in need of pain treatment, especially chronic pain treatment, are therefore at particular risk of adverse effects if they suffer from a pre-existing gastrointestinal or pulmonary disorder. Unlike traditional opioid analgesics, the compounds of the present invention provide analgesic relief without significant adverse gastrointestinal effects and without significant respiratory depression. Therefore, such compounds would provide improved safety and efficacy for patients in need of pain treatment having these preexisting GI and pulmonary disorders. In further embodiments, a compound of the present invention may be combined with a traditional opiate agent to provide improved pain control with a dose-sparing effect as to the traditional opiate agent (and concomitantly reduced risk of adverse effects).

Thus, in particular embodiments, the present invention further provides:

1.37 Method 1 or any of 1.1-1.36, wherein the patient suffers from a pre-existing or co-morbid gastrointestinal disorder and/or pulmonary disorder;

1.38 Method 1.37, wherein the pre-existing or co-morbid disorder is selected from the group consisting of irritable bowel syndrome, pelvic floor disorder, diverticulitis, inflammatory bowel disease, colon or colorectal cancer, celiac disease, non-celiac gluten sensitivity, asthma, chronic obstructive pulmonary disease (COPD), dyspnea, pneumonia, congestive heart failure, interstitial lung disease, pneumothorax, bronchitis, pulmonary embolism, and traumatic chest injury (e.g., broken sternum or ribs, bruised intercostal muscles);

1.39 Method 1.37 or 1.38 wherein the central nervous system disorder is a pain disorder, e.g., a condition associated with pain, such as cephalic pain, idiopathic pain, neuropathic pain, chronic pain (e.g., moderate to moderately severe chronic pain, for example, in patients requiring 24-hour extended treatment for other ailments), fibromyalgia, dental pain, traumatic pain, or chronic fatigue;

1.40 Any of Method 1 or 1.1-1.39, wherein the central nervous system disorder is opiate use disorder, opiate withdrawal or opiate dependency, and wherein the method provides relief from withdrawal-induced symptoms (e.g., gastrointestinal symptoms such as diarrhea, anxiety, depression, pain, sleep disturbances, or any combination thereof);

1.41 Any of Method 1 or 1.1-1.40, wherein the method further comprises the concurrent administration of another opiate or opioid agent, e.g., administered simultaneously, separately or sequentially;

1.42 Method 1.41, wherein the additional opiate or opioid agent is selected from the group consisting of morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof;

1.43 Any of Method 1 or 1.1-1.42, wherein the method further comprises the concurrent administration of a NMDA receptor antagonist, e.g., administered simultaneously, separately or sequentially;

1.44 Method 1.43, wherein the NMDA receptor antagonist is selected from the group consisting of ketamine (e.g., S-ketamine and/or R-ketamine), hydroxynorketamine, memantine, dextromethorphan, dextroallorphan, dextrorphan, amantadine, and agmatine, or any combination thereof;

1.45 Any of methods 1.37-1.44, wherein the compound is the compound of Formula I, wherein Z is —O—.

In a seventh aspect, the invention provides a method (Method 2) for the prophylaxis or treatment of one or more sleep disorders comprising administering to a patient in need thereof a Compound of Formulas I-II et seq. or a Pharmaceutical Composition 6 or 6.1-6.7 or P.1-P.7, (Method 2) for example Method 2 wherein the compound or composition administered is:

2.1 Compound I or 1.1-1.34, in free or pharmaceutically acceptable salt form;

2.2 Compound II or 2.1-2.10, in free or pharmaceutically acceptable salt form;

2.3 Compound 5 or 5.1-5.5;

2.4 a Pharmaceutical Composition as described by any of Compositions 6 and 6.1-6.7;

2.5 Depot Composition as described in Depot Composition 6.6 or 6.7;

2.6 Pharmaceutical Composition P.1-P.7;

2.7 Osmotic-controlled Release Oral Delivery System Composition as hereinbefore described;

In a further embodiment of the seventh aspect, the invention provides Method 2, or 2.1-2.7, wherein the sleep disorder includes sleep maintenance insomnia, frequent awakenings, and waking up feeling unrefreshed; for example:

2.8 Any of the foregoing methods, wherein the sleep disorder is sleep maintenance insomnia;

2.9 Any of the foregoing methods, wherein the effective amount is 1 mg-5 mg, preferably 2.5-5 mg, per day;

2.10 Any of the foregoing methods, wherein the effective amount is 2.5 mg or 5 mg, per day;

2.11 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;

2.12 Any of the foregoing methods wherein the patient suffers from Parkinson's disease.

In a further embodiment of the seventh aspect, the invention provides Method 2, or any of 2.1-2.12, wherein the sleep disorder includes sleep maintenance insomnia, frequent awakenings, and waking up feeling unrefreshed.

The Compounds of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the present disclosure may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the present disclosure in combination with one or more second therapeutic agents in free or salt form (e.g., pharmaceutically acceptable salt form), wherein the dosages of (i) the second therapeutic agent(s) or (ii) both Compound of the present disclosure and the second therapeutic agents, are lower than if the agents/compounds are administered as a monotherapy. In a particular embodiment, the Compounds of the present disclosure are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

In some further embodiments of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects, wherein the second therapeutic agent is an opiate antagonist or inverse agonist (e.g., naloxone). The Compounds of the present disclosure may be simultaneously, sequentially, or contemporaneously administered with such opiate antagonists or opiate inverse agonists.

Therefore, in an eighth aspect, the present disclosure provides Method 1, or any of Methods 1.1-1.45, or Method 2 or any of 2.1-2.12, further comprising the administration of one or more therapeutic agents to the patient, wherein the one or more therapeutic agents are selected from compounds that modulate GABA activity (e.g., enhances the activity and facilitates GABA transmission), a GABA-B agonist, a 5-HT receptor modulator (e.g., a 5-$HT_{1A}$ agonist, a 5-$HT_{2A}$ antagonist, a 5-$HT_{2A}$ inverse agonist, etc.), a melatonin receptor agonist, an ion channel modulator (e.g., blocker), a serotonin-2 receptor antagonist/reuptake inhibitor (e.g., a compound having both 5-$HT_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and opiate agonist and/or partial opiate agonist (such as a mu-, kappa- or delta-opiate receptor agonist or partial agonist), or opiate antagonist or inverse agonist (such as mu-, kappa- or delta-opiate receptor antagonist or inverse agonist), nociceptin agonist, and an antipsychotic agent, e.g., an atypical antipsychotic agent, in free or pharmaceutically acceptable salt form (Method 1-A and 2-A respectively; collectively, "Method 3"). In further embodiments of the eighth aspect, the present disclosure provides Method 1, or any of Methods 1.1-1.45, or Method 2 or any of 2.1-2.12, further comprising the administration to the patient of one or more therapeutic agents selected from the foregoing and further selected from agonists or partial agonists or antagonists or inverse agonists of the mu-opiate, kappa-opiate, delta-opiate, and/or nociceptin/orphanin receptors. In further embodiments of the tenth aspect, the present disclosure also provides Method 1, or any of Methods 1.1-45, or Method 2 or any of 2.1-2.12, further comprising the administration to the patient of one or more therapeutic agents selected from a serotonin HT6 receptor antagonist, and an mGluR-2, -3 or -5 receptor agonist or antagonist (including both positive and negative modulators and partial agonists).

In a further embodiment of the eighth aspect, the invention provides Method 3 (i.e., Method 1-A or 2-A), further comprising the administration to the patient of one or more therapeutic agents, as follows:

3.1 Method 1-A or 2-A, wherein the therapeutic agent(s) is compounds that modulate GABA activity (e.g., enhances the activity and facilitates GABA transmission);

3.2 Method 1-A or 2-A or 3.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals) and estazolam;

3.3 Method 1-A or 2-A, wherein the therapeutic agent is an additional 5HT2a receptor antagonist;

3.4 Method 1-A or 2-A or 3.3, wherein said additional 5HT2a receptor antagonist is selected from one or more of pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), and AVE8488 (Sanofi-Aventis, France);

3.5 Method 1-A or 2-A, wherein the therapeutic agent is a melatonin receptor agonist;

3.6 Method 1-A or 2-A or 3.5, wherein the melatonin receptor agonist is selected from a group consisting of one or more of melatonin, ramelteon (ROZEREM®, Takeda Pharmaceuticals, Japan), VEC-162 (Vanda Pharmaceuticals, Rockville, MD), PD-6735 (Phase II Discovery) and agomelatine;

3.7 Method 1-A or 2-A, wherein the therapeutic agent is an ion channel blocker;

3.8 Method I-A or 2-A or 3.7, wherein said ion channel blocker is one or more of lamotrigine, gabapentin and pregabalin.

3.9 Method 1-A or 2-A, wherein the therapeutic agent is an orexin receptor antagonist;

3.10 Method 1-A or 2-A or 3.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

3.11 Method 1-A or 2-A, wherein the therapeutic agent is the serotonin-2 receptor antagonist/reuptake inhibitor (SARI);

3.12 Method 1-A or 2-A or 3.11, wherein the serotonin-2 receptor antagonist/reuptake inhibitor (SARI) is selected from a group consisting of one or more Org 50081 (Organon-Netherlands), ritanserin, nefazodone, serzone and trazodone;

3.13 Method 1-A or 2-A, wherein the therapeutic agent is the 5HTIa agonist;

3.14 Method 1-A or 2-A or 3.13, wherein the 5HTIa agonist is selected from a group consisting of one or more of repinotan, sarizotan, eptapirone, buspirone and MN-305 (MediciNova, San Diego, CA);

3.15 Method 1-A or 2-A, wherein the therapeutic agent is the neurokinin-1 drug;

3.16 Method 1-A or 2-A or 3.15, wherein the neurokinin-1 drug is Casopitant (GlaxoSmithKline);

3.17 Method 1-A or 2-A, wherein the therapeutic agent is an antipsychotic agent;

3.18 Method 1-A or 2-A or 3.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.19 Method 1-A or 2-A, wherein the therapeutic agent is an anti-depressant;

3.20 Method 1-A or 2-A or 3.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine;

3.21 Method 1-A or 2-A, 3.17 or 3.18, wherein the antipsychotic agent is an atypical antipsychotic agent;

3.22 Method 1-A or 2-A, or any of 3.17-3.21, wherein the atypical antipsychotic agent is selected from a group consisting of brexpiprazole, cariprazine, asenapine, lurasidone, clozapine, aripiprazole, olanzapine, quetiapine, risperidone, ziprasidone, and paliperidone;

3.23 Method 1-A or 2-A, wherein the therapeutic agent is selected from any of methods 3.1-3.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam, pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.24 Method 1-A or 2-A wherein the therapeutic agent is an H3 agonist;

3.25 Method 1-A or 2-A, wherein the therapeutic agent is an H3 antagonist;

3.26 Method 1-A or 2-A, wherein the therapeutic agent is a noradrenergic agonist or antagonist;

3.27 Method 1-A or 2-A, wherein the therapeutic agent is a galanin agonist;

3.28 Method 1-A or 2-A, wherein the therapeutic agent is a CRH antagonist;

3.29 Method 1-A or 2-A, wherein the therapeutic agent is a human growth hormone;

3.30 Method 1-A or 2-A, wherein the therapeutic agent is a growth hormone agonist;

3.31 Method 1-A or 2-A, wherein the therapeutic agent is estrogen;

3.32 Method 1-A or 2-A, wherein the therapeutic agent is an estrogen agonist;

3.33 Method 1-A or 2-A, wherein the therapeutic agent is a neurokinin-1 drug;

3.34 Method 1-A or 2-A, wherein a therapeutic agent is combined with compounds of Formula (I) and the therapeutic agent is an anti-Parkinson agent such as L-dopa, co-careldopa, duodopa, stalevo, Symmetrel, benztropine, biperiden, bromocriptine, entacapone, pergolide, pramipexole, procyclidine, ropinirole, selegiline and tolcapone;

3.35 Method 1-A or 2-A, wherein the therapeutic agent is an opiate agonist or partial opiate agonist, for example, a mu-agonist or partial agonist, or a kappa-agonist or partial agonist, including mixed agonist/antagonists (e.g., an agent with partial mu-agonist activity and kappa-antagonist activity);

3.36 Method 3.35, wherein the therapeutic agent is buprenorphine, optionally, wherein said method does not include co-treatment with an anxiolytic agent, e.g., a GABA compound or benzodiazepine;

3.37 Method 1-A or 2-A, wherein compounds of Formula (I) may be used to treat sleep disorders, depression, psychosis, or any combinations thereof, in patients suffering from the listed diseases and/or Parkinson's disease;

3.38 Method 1-A or 2-A, wherein the disorder is selected from at least one or more of psychosis, e.g., schizophrenia, depression, mood disorders, sleep disorders (e.g., sleep maintenance and/or sleep onset) or any combination of disorders thereof;

3.39 Method 1-A or 2-A, wherein the therapeutic agent(s) is an opiate receptor antagonist or inverse agonist, e.g., a full opiate antagonist, for example, selected from naloxone, naltrexone, nalmefene, methadone, nalorphine, levallorphan, samidorphan, nalodeine, cyprodime, or norbinaltorphimine;

3.40 Any of the foregoing methods wherein the disorder is sleep disorder;

3.41 Any of the foregoing methods, wherein the disorder is sleep disorder associated with psychosis, e.g., schizophrenia or Parkinson's disease; in free or pharmaceutically acceptable salt form.

In a ninth aspect of the invention, the combination of a Compound of the present disclosure and one or more second therapeutic agents as described in Methods 1-A, 2-A or any of Methods 3 or 3.1-3.41 may be administered to the patient as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods 1-A, 2-A, 3 or 3.1-3.41 comprises administering to the patient in need thereof, a Compound of the Invention in combination with an atypical antipsychotic agent, e.g., a compound selected from brexpiprazole, cariprazine, asenapine, lurasidone, clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods 1-A, 2-A, 3 or 3.1-3.41 comprises administering to the patient in need thereof, a Compound of the Invention in combination with an anti-depressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compound of the Invention.

In still another embodiment, Methods 1-A, 2-A, 3 or 3.1-3.41 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam or any combinations thereof, in free or pharmaceutically acceptable salt form. In other embodiments, the methods disclosed herein do not further comprise administration of an GABA compound, a benzodiazepine or any other anxiolytic agent.

In another preferred embodiment, Methods 1-A, 2-A, 3 or 3.1-3.41 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods 1-A, 2-A, 3 or 3.1-3.41 comprises administering to a patient in need thereof, a Compound of the Invention in combination (including as part of a daily dosage regimen) with an atypical stimulant, e.g., a modafinil, adrafinil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In another embodiment, Methods 1-A, 2-A, 3 or 3.1-3.41 comprises administering to a patient in need thereof, a Compound of the Invention in combination (including as part of a daily dosage regimen) with an opiate receptor antagonist or inverse agonist, e.g., a full opiate antagonist, for example, selected from naloxone, naltrexone, nalmefene, methadone, nalorphine, levallorphan, samidorphan, nalodeine, cyprodime, or norbinaltorphimine.

In some of the foregoing embodiments, each of the Compounds of Formulas I-II et seq.; Pharmaceutical Compositions 6 and 6.1-6.5; Depo Compositions 6.6 and 6.7; Compositions P.1-P.7; Methods 1 and 1.1-1.45; and Methods 2 and 2.1-2.12; the compound of the present disclosure is substantially free of compound of the compound of Formula A and/or substantially free of the compound of Formula B.

In a tenth aspect, the invention provides use of a compound as described in the following:
- 11.1 Compound I or 1.1-1.34, in free or pharmaceutically acceptable salt form;
- 11.2 Compound II or 2.1-2.10, in free or pharmaceutically acceptable salt form;
- 11.3 Compound 5 or 5.1-5.5;
- 11.4 Pharmaceutical Composition 6 and 6.1-6.7;
- 11.5 Pharmaceutical Composition P.1-P.7;
- 11.6 Osmotic-controlled Release Oral Delivery System Composition as hereinbefore described;

(in the manufacture of a medicament) for the treatment or prophylaxis of one or more disorders as disclosed hereinbefore, e.g., in any of Method 1 or 1.1-1.45, any of Method 2 and 2.1-2.12, and Method 3 or 3.3-3.41, or any methods described in the eleventh aspect of the invention.

In the eleventh aspect, the invention provides a pharmaceutical composition as hereinbefore described, e.g.:
- 12.1 Pharmaceutical Composition 6 and 6.1-6.7;
- 12.2 Pharmaceutical Composition P.1-P.7;
- 12.3 Osmotic-controlled Release Oral Delivery System Composition as hereinbefore described,
- for use in the treatment or prophylaxis of one or more disorders as disclosed hereinbefore, e.g., in any of Methods 1 and 1.1-1.33, Methods 2 and 2.1-2.12, Methods I-A, II-A, 3 or 3.1-3.41 or any methods described in the ninth or tenth aspects of the invention.

DETAILED DESCRIPTION OF THE INVENTION

If not otherwise specified or clear from context, the following terms as used herein have the following meetings:

The compounds of the present disclosure have biologically labile functional groups positioned within the compounds such that natural metabolic activity will remove the labile functional groups, resulting in the Compound of Formula A and/or the Compound of Formula B. As such, administration of the compounds of the present disclosure to a patient in need thereof result in a both immediate and delayed release to the tissues of said person the Compound of Formula A and/or the Compound of Formula B. It is expected that compounds of the present disclosure do not have significant pharmacologic activity in themselves, but will serve as a reservoir of the pharmacologically active compounds of Formula A and/or Formula B. In this way, the compounds of the present disclosure are particularly suited to formulation as long-acting injectable (LAI) or "Depot" pharmaceutical compositions. Without being bound by theory, an injected "depot" comprising a compound of the present disclosure will gradually release into the body tissues said compound, in which tissues said compound will be gradually metabolized to yield a compound of Formula A and/or compound of Formula B. Such depot formulations may be further adjusted by the selection of appropriate components to control the rate of dissolution and release of the compounds of the present disclosure.

The Compounds of Formula A and B have been showed to have a variety of useful pharmaceutical properties, each of which is expected to be shared by the compounds of the present disclosure. For example, the compound of Formula A and B have potent 5-$HT_{2A}$, $D_1$ and Mu opiate antagonism, along with moderate $D_1$, $D_2$ and SERT antagonism. Furthermore, it has been unexpectedly found that such compounds may operate as "biased" Mu opiate ligands. This means that when the compounds bind to Mu opiate receptors, they may operate as partial Mu agonists via G-protein coupled signaling, but as Mu antagonists via beta-arrestin signaling. This is in contrast to the traditional opiate agonists morphine and fentanyl, which tend to strongly activate both G-protein signaling and beta-arrestin signaling. The activation of beta-arrestin signaling by such drugs is thought to mediate the gastrointestinal dysfunction and respiratory suppression typically mediated by opiate drugs. Compounds according to the present invention, in particular compounds according to Formula I, are therefore expected to result in pain amelioration with less severe gastrointestinal and respiratory side effects than existing opiate analgesics. This effect has been shown in pre-clinical studies and Phase II and Phase III clinical trials of the biased Mu agonist oliceridine. Oliceridine has been shown to result in biased mu agonism via G-protein coupled signaling with reduced beta-arresting signaling compared to morphine, and this has been linked to its ability to produce analgesia with reduced respiratory side effects compared to morphine. Furthermore, because these compounds antagonize the beta-arrestin pathway, they are expected to be useful in treating opiate overdose, because they will inhibit the most severe opiate adverse effects while still providing pain relief. Furthermore, these compounds also have sleep maintenance effect due to their serotonergic activity. As many people suffering from chronic pain have difficulty sleeping due to the pain, these compounds can help such patients sleep through the night due to the synergistic effects of serotonergic and opiate receptor activities.

Thus, in certain embodiments, the Compounds of the present disclosure may be used in a method of treating opiate use disorder (OUD), opiate overdose, or opiate withdrawal, either alone, or in conjunction with an opiate antagonist or inverse agonist (e.g., naloxone or naltrexone). Compounds of the present disclosure are expected to show a strong ability to mitigate the dysphoria and psychiatric comorbidities associated with drug withdrawal (e.g., mood and anxiety disorders, sleep disturbances), and it also provides potent analgesia but without the adverse effects (e.g., GI effects and pulmonary depression) and abuse potential seen with other opioid treatments (e.g., oxycodone, methadone or buprenorphine). The unique pharmacologic profile of these compounds should also mitigate the risks of adverse drug-drug interactions (e.g., alcohol). These compounds are therefore particularly suited to treat opiate use disorder and the symptoms associated with opiate withdrawal. In addition, to the compounds' direct effect on mu receptor activity, the compounds' effect on serotonergic pathways results in antidepressant, sleep maintenance, and anxiolytic effects. Because depression and anxiety are key factors leading susceptible patients to opioid use in the first place, the compounds of the present disclosure would both reduce the symptoms of opiate withdrawal at the same time that they reduce the psychiatric co-morbidities which promote opioid use—a two-pronged strategy to reduce the risk of remission. The sleep maintenance provided by these compounds would further improve the quality of life of patients undergoing OUD treatment.

"Alkyl" as used herein is a saturated or unsaturated hydrocarbon moiety, e.g., one to twenty-one carbon atoms in length, unless indicated otherwise; any such alkyl may be linear or branched (e.g., n-butyl or tert-butyl), preferably linear, unless otherwise specified. For example, "$C_{1-21}$alkyl" denotes alkyl having 1 to 21 carbon atoms. In one embodiment, alkyl is optionally substituted with one or more hydroxy or $C_{1-22}$ alkoxy (e.g., ethoxy) groups. In another embodiment, alkyl contains 1 to 21 carbon atoms, preferably straight chain and optionally saturated or unsaturated, for example in some embodiments wherein $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan.

Unless otherwise indicated, the Compounds of the present disclosure, e.g., Compound I or 1.1-1.34, Compound II or 2.1-2.10 (collectively, Compounds of Formulas I-II et seq.) may exist in free or salt, e.g., as acid addition salts, form. An acid-addition salt of a compound of the invention which is sufficiently basic, for example, an acid-addition salt with, for example, an inorganic or organic acid, for example hydrochloric, hydrobromic, sulfuric, phosphoric, acid acetic, trifluoroacetic, citric, maleic acid, toluene sulfonic, propionic, succinic, glycolic, stearic, lactic, malic, tartaric, citric, ascorbic, pamoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition, a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the Compounds of the Invention is a toluenesulfonic acid addition salt. In another particular embodiment, the salt of the Compounds of the Invention is a fumaric acid addition salt. In a particular embodiment, the salt of the Compounds of the Invention is a phosphoric acid addition salt.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included within the scope of the compounds of the present disclosure.

The Compounds of the present disclosure may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$ $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention. In addition, the substitution of atoms of having the natural isotopic distributing with heavier isotopes can result in desirable change in pharmacokinetic rates when these substitutions are made at metabolically liable sites. For example, the incorporation of deuterium ($^2H$) in place of hydrogen can slow metabolic degradation when the position of the hydrogen is a site of enzymatic or metabolic activity.

Compounds of the present disclosure may be included as a depot formulation, e.g., by dispersing, dissolving or encapsulating the Compounds of the Invention in a polymeric matrix as described in any of Composition 6 and 6.1-6.7, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-1-alanine, poly-.gamma.-benzyl-1-glutamic acid or poly-y-methyl-1-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-1-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e.g., glucose or, e.g., mannitol. These esters are known and described in GB 2,145,422 and in U.S. Pat. No. 5,538,739, the contents of which are incorporated by reference.

The star polymers may be prepared using polyhydroxy compounds, e.g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d,l-lactide-co-glycolide) have a central glucose moiety having rays of linear polylactide chains.

The depot compositions of the invention (e.g., Compositions 6 and 6.1-6.10, in a polymer matrix) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the present disclosure incorporated in the microparticles usually ranges from about 1 wt % to about 90 wt. %, preferably 30 to 50 wt. %, more preferably 35 to 40 wt. %. By weight % is meant parts of the Compounds of the present disclosure per total weight of microparticle.

The pharmaceutical depot compositions may comprise a pharmaceutically-acceptable diluent or carrier, such as a water miscible diluent or carrier.

Details of Osmotic-controlled Release Oral Delivery System composition may be found in EP 1 539 115 (U.S. Pub. No. 2009/0202631) and WO 2000/35419 (US 2001/0036472), the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally. In certain embodiments, the Compounds of the Invention, e.g., in depot formulation, is preferably administered parenterally, e.g., by injection, for example, intramuscular or subcutaneous injection.

In general, satisfactory results for Method 1 and 1.1-1.45, Method 2 and 2.1-2.12, and Method 3 and 3.1-3.41, or use of the Compounds of the present disclosure as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; (4) sleep disorders associated with psychosis, e.g., schizophrenia, or Parkinson's disease; and (5) substance addiction, substance use disorders and/or substance-induced disorders, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration.

Satisfactory results for Method 2 or 2.1-2.12 or use of the Compounds of the present disclosure as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

Satisfactory results for Method 1-A or Method 2-A, or any of 3.1-3.41 are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 3.1-3.41 are indicated to be obtained at less than 5 mg, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the present disclosure may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069 (each equivalent to US 2011/112105).

Pharmaceutical compositions comprising Compounds of the present disclosure may be prepared using conventional diluents or excipients (an example include, but is not limited to sesame oil) and techniques known in the galenic art. Thus, oral dosage forms may include tablets, capsules, solutions, suspensions and the like.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration Methods of Making the Compounds of the Invention The Compound of Formula A, and methods for its synthesis, have been disclosed in International Application PCT/US2017/15178, publishing as WO 2017/132408 and in US 2017/319580. The Compounds of the present disclosure, wherein Z is —O—, may be prepared, for example, by reacting the Compound of Formula A with a suitable alkylating and acylating agents, as appropriate, in accordance with Scheme 1 below. Other methods for carrying out similar transformations are known to those skilled in the art.

Scheme 1

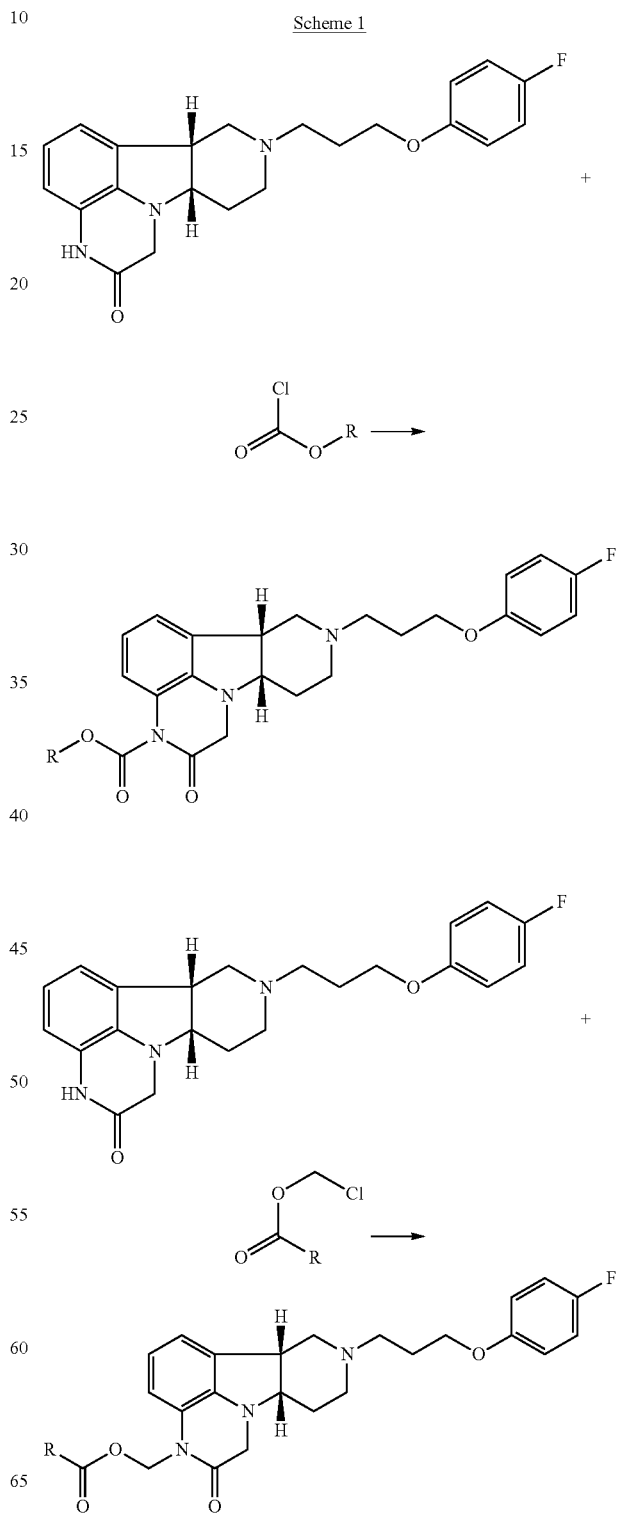

-continued

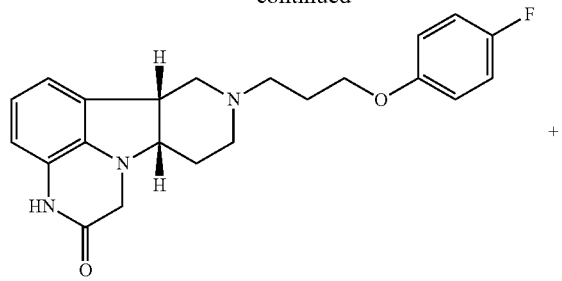

+

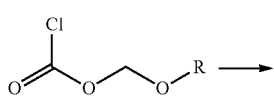

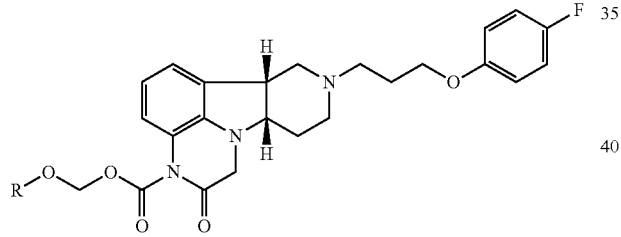

Other Compounds of the present disclosure came be made by analogous procedures known to those skilled in the art.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Salts of the Compounds of the present disclosure may be prepared as similarly described in U.S. Pat. Nos. 6,548,493; 7,238,690; 6,552,017; 6,713,471; 7,183,282; RE39,680; RE39,679; and WO 2009/114181 (US 2011/112105), the contents of each of which are incorporated by reference in their entirety.

Diastereomers of prepared compounds can be separated by, for example, HPLC using CHIRALPAK® AY-H, 5μ, 30×250 mm at room temperature and eluted with 10% ethanol/90% hexane/0.1% dimethylethylamine Peaks can be detected at 230 nm to produce 98-99.9% ee of the diastereomer.

Example 1: Synthesis of 4-((6bR,10aS)-2-oxo-2,3, 6b,9,10,10a-hexahydro-1H,7H-pyrido[3',4':4,5]pyrrolo[1,2,3-de]quinoxalin-8-yl-1-(4-fluoro-phenyl)-butan-1-one

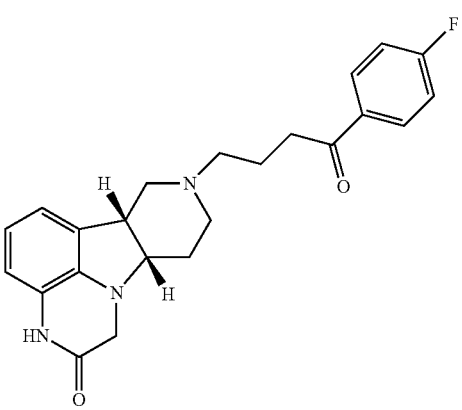 [SMILES: O=C1CN2c3c(cccc3[C@@H]3CN(CCCC(=O)c4ccc(F)cc4)CC[C@@H]32)N1]

(6bR,10aS)-2-oxo-2,3,6b,9,10,10a-hexahydro-1H,7H-pyrido[3',4'4,5]pyrrolo[1,2,3-de]quinoxaline-8-carboxylic acid ethyl ester (6.4 g, 21.2 mmol) is suspended in HBr acetic acid solution (64 mL, 33% w/w) at room temperature. The mixture is heated at 50° C. for 16 h. After cooling, and treatment with ethyl acetate (300 mL), the mixture is filtered. The filter cake is washed with ethyl acetate (300 mL), and then dried under vacuum. The obtained HBr salt is then suspended in methanol (200 mL), and cooled with dry ice in isopropanol. Under vigorous stirring, ammonia solution (10 mL, 7N in methanol) is added slowly to the suspension to adjust the pH of the mixture to 10. The obtained mixture is dried under vacuum without further purification to give crude (6bR,10aS)-2-oxo-2,3,6b,9,10,10a-hexahydro-1H, 7H-pyrido[3',4':4,5]pyrrolo[1,2,3-de]quinoxaline (8.0 g), which is used directly in the next step. MS (ESI) m/z 230.2 [M+H]$^+$.

The crude (6bR,10aS)-2-oxo-2,3,6b,9,10,10a-hexahydro-1H,7H-pyrido[3',4':4,5]pyrrolo[1,2,3-de]quinoxaline (1.4 g)

is dissolved in DMF (14 mL), and then KI (2.15 g) and 4-Chloro-4'-fluorobutyrophenone (2 mL) are added successively. The mixture is degassed with argon, followed by adding N,N-diisopropylethylamine (DIPEA, 2 mL). The mixture is heated at 78° C. for 2 h. After cooling, the solvents are removed under reduced pressure. The dark brown residue is suspended in dichloromethane (100 mL) and then extracted with water (30 mL). The organic layer is separated, and dried over $K_2CO_3$. After filtration, the solvents are removed under reduced pressure. The obtained crude product is purified by silica gel column chromatography eluting with 0-10% of methanol in ethyl acetate containing 0.1% of 7N ammonia in methanol to yield 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one as a light yellow solid (767 mg). $^1$H NMR (500 MHz, DMSO-$d_6$) δ 10.3 (s, 1H), 8.1-8.0 (m, 2H), 7.3 (dd, J=8.86 Hz, 2H), 6.8 (d, J=7.25 Hz, 1H), 6.6 (dd, J=7.55 Hz, 1H), 6.6 (d, J=7.74 Hz, 1H), 3.8 (d, J=14.49 Hz, 1H), 3.3-3.3 (m, 1H), 3.2-3.2 (m, 1H), 3.1-3.0 (m, 1H), 3.0 (t, J=6.88 Hz, 2H), 2.8-2.8 (m, 1H), 2.6-2.5 (m, 1H), 2.3-2.2 (m, 2H), 2.1-2.0 (m, 1H), 1.9-1.8 (m, 1H), 1.8 (t, J=6.99 Hz, 2H), 1.6 (t, J=11.25 Hz, 2H). MS (ESI) m/z 394.2 [M+H]+.

Example 2: Synthesis of (6bR,10aS)-8-(3-(4-fluoro-phenoxy)propyl)-6b,7,8,9,10,10a-hexahydro-1H-pyrido[3',4':4,5]pyrrolo[1,2,3-de]quinoxalin-2(3H)-one A mixture of (6bR,10aS)-6b,7,8,9,10,10a-hexahydro-1H-pyrido[3',4':4,5]pyrrolo[1,2,3-de]quinoxalin-2(3H)-one (100 mg, 0.436 mmol), 1-(3-chloroproxy)-4-fluorobenzene (100 μL, 0.65 mmol) and KI (144 mg, 0.87 mmol) in DMF (2 mL) is degassed with argon for 3 minutes and DIPEA (150 μL, 0.87 mmol) is added. The resulting mixture is heated to 78° C. and stirred at this temperature for 2 h. The mixture is cooled to room temperature and then filtered. The filter cake is purified by silica gel column chromatography using a gradient of 0-100% ethyl acetate in a mixture of methanol/7N $NH_3$ in methanol (1:0.1 v/v) as an eluent to produce partially purified product, which is further purified with a semi-preparative HPLC system using a gradient of 0-60% acetonitrile in water containing 0.1% formic acid over 16 min to obtain the title product as a solid (50 mg, yield 30%). MS (ESI) m/z 406.2 [M+1]+. $^1$H NMR (500 MHz, DMSO-$d_6$) δ 10.3 (s, 1H), 7.2-7.1 (m, 2H), 7.0-6.9 (m, 2H), 6.8 (dd, J=1.03, 7.25 Hz, 1H), 6.6 (t, J=7.55 Hz, 1H), 6.6 (dd, J=1.07, 7.79 Hz, 1H), 4.0 (t, J=6.35 Hz, 2H), 3.8 (d, J=14.74 Hz, 1H), 3.3-3.2 (m, 3H), 2.9 (dd, J=6.35, 11.13 Hz, 1H), 2.7-2.6 (m, 1H), 2.5-2.3 (m, 2H), 2.1 (t, J=11.66 Hz, 1H), 2.0 (d, J=14.50 Hz, 1H), 1.9-1.8 (m, 3H), 1.7 (t, J=11.04 Hz, 1H).

Example 3: Cellular and Nuclear Receptor Functional Assays

Cellular and Nuclear Receptor Functional Assays are performed on the compound of Example 1 according to the procedure of Wang, J. B. et al. (1994), *FEBS Lett.*, 338:217-222. The compound is tested at several concentrations to determine $IC_{50}$ or $EC_{50}$. Cellular agonist effects are calculated as percent of control response to a known reference agonist for each target and cellular antagonist effect is calculated as a percent inhibition of control reference agonist response for each target.

The following assay is performed to determine the effect of the Compound of Example 1 on the μ (MOP) (h) receptor:

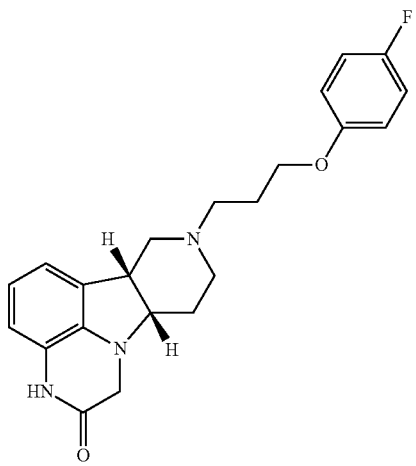 [SMILES: O=C1CN2c3c(cccc3[C@@H]3CN(CCCOc4ccc(F)cc4)CC[C@@H]32)N1]

| Assay (Receptor) | Source | Stimulus | Incubation | Measured Component | Detection Method |
|---|---|---|---|---|---|
| μ (MOP) (h) (agonist effect) | human recombinant MOP receptor (CHO cells) | none (0.3 μM DAMGO for control) | 10 min @ 37° C. | cAMP | HTRF |
| μ (MOP) (h) (antagonist effect) | human recombinant MOP receptor (CHO cells) | DAMGO (20 nM) | 10 min @ 37° C. | cAMP | HTRF |

For the antagonists, the apparent dissociation constants ($K_B$) are calculated using the modified Cheng Prusoff equation:

$$K_B = \frac{IC_{50}}{1 + (A/EC_{50A})}$$

where A=concentration of reference agonist in the assay, and $EC_{50A}=EC_{50}$ value of the reference agonist.

The compound of Example 1 is found to have a µ (MOP) (h) (antagonist effect) with an $IC_{50}$ of $1.3 \times 10^{-6}$ M; and a $K_B$ of $1.4 \times 10^{-7}$ M.

The agonist activity results are expressed as a percent of control agonist response:

$$\frac{\text{measured response}}{\text{control response}} \times 100$$

and antagonist activity as a percent inhibition of control agonist maximum response:

$$100 - \left( \frac{\text{measured response}}{\text{control response}} \times 100 \right)$$

obtained in the presence of the Compound of Example 1.

The $EC_{50}$ values (concentration producing a half-maximal response) and $IC_{50}$ values (concentration causing a half-maximal inhibition of the control agonist response) are determined by non-linear regression analysis of the concentration-response curves generated with mean replicate values using Hill equation curve fitting:

$$Y = D + \left[ \frac{A - D}{1 + (C/C_{50})^{nH}} \right]$$

where Y=response, A=left asymptote of the curve, D=right asymptote of the curve, C=compound concentration, and $C_{50}=EC_{50}$ or $IC_{50}$, and nH=slope factor. The analysis is performed using software developed in-house and validated by comparison with data generated by the commercial software SigmaPlot® 4.0 for Windows® (© 1997 by SPSS Inc.).

Example 4: Receptor Binding Profile

Receptor binding is determined for the Compounds of Example 1 and 2. The following literature procedures are used, each of which reference is incorporated herein by reference in their entireties: 5-HT$_{2A}$: Bryant, H. U. et al. (1996), *Life Sci.*, 15:1259-1268; D2: Hall, D. A. and Strange, P. G. (1997), *Brit. J. Pharmacol.*, 121:731-736; D1: Zhou, Q. Y. et al. (1990), *Nature*, 347:76-80; SERT: Park, Y. M. et al. (1999), *Anal. Biochem.*, 269:94-104; Mu opiate receptor: Wang, J. B. et al. (1994), *FEBS Lett.*, 338:217-222.

In general, the results are expressed as a percent of control specific binding:

$$\frac{\text{measured specific binding}}{\text{control specific binding}} \times 100$$

and as a percent inhibition of control specific binding:

$$100 - \left( \frac{\text{measured specific binding}}{\text{control specific binding}} \times 100 \right)$$

obtained in the presence of the test compounds.

The $IC_{50}$ values (concentration causing a half-maximal inhibition of control specific binding) and Hill coefficients (nH) are determined by non-linear regression analysis of the competition curves generated with mean replicate values using Hill equation curve fitting:

$$Y = D + \left[ \frac{A - D}{1 + (C/C_{50})^{nH}} \right]$$

where Y=specific binding, A=left asymptote of the curve, D=right asymptote of the curve, C=compound concentration, $C_{50}=IC_{50}$, and nH=slope factor. This analysis was performed using in-house software and validated by comparison with data generated by the commercial software SigmaPlot® 4.0 for Windows® (© 1997 by SPSS Inc.). The inhibition constants (Ki) were calculated using the Cheng Prusoff equation:

$$Ki = \frac{IC_{50}}{(1 + L/K_D)}$$

where L=concentration of radioligand in the assay, and $K_D$=affinity of the radioligand for the receptor. A Scatchard plot is used to determine the $K_D$.

The following receptor affinity results are obtained:

| | Ki (nM) or maximum inhibition | |
|---|---|---|
| Receptor | Example 1 | Example 2 |
| 5-HT$_{2A}$ | 11 | 8.3 |
| D2 | 47% inhibition at 240 nM | 160 |
| D1 | 22 | 50 |
| SERT | 44% inhibition at 240 nM | 590 |
| Mu opiate receptor | 22 | 11 |
| Delta opioid | | No inhibition |
| Kappa opioid | | 16% @ 100 nM |
| NOP (Nociceptin Receptor) | | No inhibition |

Example 5: DOI-Induced Head Twitch Model in Mice

R—(−)-2,5-dimethoxy-4-iodoamphetamine (DOI) is an agonist of the serotonin 5-HT$_2$ receptor family. When administered to mice, it produces a behavioral profile associated with frequent head twitches. The frequency of these head twitches during a predetermined period of time can be taken as an estimate of 5-HT$_2$ receptor agonism in the brain. Conversely, this behavioral assay can be used to determine 5-HT$_2$ receptor antagonism in the brain by administering the DOI with or without an antagonist and recording the reduction in DOI-induced head twitches after the administration of the antagonist.

The method of Darmani et al., *Pharmacol Biochem Behav*. (1990) 36:901-906 (the contents of which are incorporated by reference in their entirety) is used with some modifications. (±)-DOI HCl is injected subcutaneously and the mice are immediately placed in a conventional plastic cage. The number of head twitches is counted during 6 min, beginning 1 min after DOI administration. The tested compound is administered orally 0.5 hr before the injection of DOI. Results area calculated as the EC50 for reducing DOI-induced head twitches. The results are shown in the following Table:

| Compound | $EC_{50}$ (mg/kg, p.o.) |
|---|---|
| Example 1 | 0.23 |
| Example 2 | 0.44 |

The results show that the compounds of Example 1 and 2 potently block DOI head twitch, consistent with the in-vitro 5-$HT_{2A}$ results shown in Example 4.

Example 6: Mouse Tail Flick Assay

The Mouse Tail Flick Assay is a measure of analgesia, indicated by the pain reflex threshold of restrained mice. Male CD-1 mice are positioned with their tails under a focused beam of a high-intensity infrared heat source, resulting in heating of the tail. The animal can withdraw its tail from the heat source at any time that it becomes uncomfortable. The amount of time (latency) between turning on the heating instrument and the flicking of the mouse's tail out of path of the heat source is recorded. Administration of morphine results in analgesia, and this produces a delay in the mouse's reaction to the heat (increased latency). Prior administration of a morphine receptor (MOR) antagonist, i.e., naloxone (NAL), reverses the effect and results in normal latency time. This test is used as a functional assay to gauge antagonism of mu-opiate receptors.

Example 6a: Antagonism of Morphine-Induced Analgesia by Compounds of Examples 1 and 2

Ten male CD-1 mice (about 8 weeks of age) are assigned to each of five treatment groups. The groups are treated as follows: Group (1) [negative control]: administered 0.25% methylcellulose vehicle p.o., 60 minutes before the tail flick test, and saline vehicle 30 minutes before the tail flick test; Group (2) [positive control]: administered 0.25% methylcellulose vehicle p.o., 60 minutes before the test, and 5 mg/kg morphine in saline 30 minutes before the test; Group (3) [positive control]: administered 3 mg/kg naloxone in saline 50 minutes before the test, and 5 mg/kg morphine in saline 30 minutes before the test; Groups (4)-(6): administered either 0.1 mg/kg, 0.3 mg/kg or 1 mg/kg of the test compound in 0.25% methylcellulose vehicle p.o., 60 minutes before the test, and 5 mg/kg morphine in 30 minutes before the test. The experiment is repeated for the compounds of Example 1 and Example 2. The results are shown in the following table as mean latency measured in seconds:

|  | Group 1 Veh/Veh | Group 2 Veh/Mor | Group 3 Nal/Mor | Group 4 Cmpd/Mor (0.1 mg/kg) | Group 5 Cmpd/Mor (0.3 mg/kg) | Group 6 Cmpd/Mor (1 mg/kg) |
|---|---|---|---|---|---|---|
| Ex. 1 | 1.028 | 9.361 | 2.496 | 8.870 | 6.907 | 6.240 |
| Ex. 2 | 0.887 | 8.261 | 3.013 | 6.947 | 5.853 | 6.537 |

The results demonstrate that the compounds of Example 1 and Example 2 both exert a dose-dependent blockade of morphine-induced mu-opiate receptor activity.

Example 6b: Analgesia by Compound of Example 2, Inhibited by Naloxone

In a second study using the mouse tail flick assay as described above, the compound of Example 2 is further compared at doses of 1.0 mg/kg, 3.0 mg/kg and 10 mg/kg against morphine at 5 mg/kg with and without pre-dosing with naloxone at 3 mg/kg (intraperitoneal). In the pre-treatment groups, the naloxone is administered 20 minutes prior to the tail flick test. In the non-pre-treatment controls, saline is administered 20 minutes prior to the tail flick test. In each group, the vehicle, morphine or compound of Example 2 is administered 30 minutes before the tail flick test. The results are shown in the table below as mean latency in seconds:

|  | Vehicle | Morphine | Ex. 2 at 1 mg/kg | Ex. 2 at 3 mg/kg | Ex. 2 at 10 mg/kg |
|---|---|---|---|---|---|
| Saline pre-treatment | 0.9 | 9.8 | 4.1 | 7.4 | 9.8 |
| Naloxone pre-treatment | 0.8 | 1.5 | 1.3 | 1.7 | 2.1 |

It is found that administration of the compound of Example 2 at all doses significantly increased the latency to tail flick, and that this effect is attenuated by pre-treatment with naloxone. This result demonstrates a dose-dependent analgesic effect produced by the Compound of Example 2, and further suggests that this effect is mediated by mu-opioid receptor agonism.

Example 6c: Time Course for Analgesia, Compound of Example 2

The tail flick assay as described above is repeated to determine the time course of analgesia resulting from administration of the compound of Example 2. Mice are administered s.c. either (1) vehicle 30 minutes prior to assay, (2) 5 mg/kg morphine 30 minutes prior to assay, or (3)-(7) the 1 mg/kg of compound of Example 3 30 minutes, 2 hours, 4 hours, 8 hours or 24 hours prior to assay. The results are shown in the table below as mean latency in seconds:

| Treatment | TF Latency (s) |
|---|---|
| Vehicle, 30 min prior | 1.30 |
| Morphine, 30 min prior | 7.90 |
| Cmpd. Ex. 2, 30 min prior | 5.77 |
| Cmpd. Ex. 2, 2 h prior | 2.42 |

-continued

| Treatment | TF Latency (s) |
|---|---|
| Cmpd. Ex. 2, 4 h prior | 1.48 |
| Cmpd. Ex. 2, 6 h prior | 1.36 |
| Cmpd. Ex. 2, 24 h prior | 1.29 |

The results show that the Compound of Example 2 produces effective analgesia when administered 30 minutes or 2 hours prior to the tail flick assay (ANOVA, P<0.001 vs. vehicle). When administered 4 hours, 8 hours, or 24 hours prior to the tail flick assay, the compound of Example 2 at 1 mg/kg does not produce an analgesic effect significantly different from the vehicle control. Thus, the compound of Example 2 does not produce prolonged analgesia, which means that it would have a lower potential for abuse and a lower risk of drug-drug interactions compared to other opiate analgesics.

Example 6d: Analgesia from Chronic Administration of the Compound of Example 2

The tail flick assay described above is repeated using a test model in which animals receive a 14-day chronic treatment regimen, followed by an acute treatment 30 minutes prior to the tail flick assay. The mice are divided into three broad groups with six sub-groups of 10 mice each. The three groups receive as the chronic treatment either (A) vehicle, (B) compound of Example 2 at 0.3 mg/kg, or (C) compound of Example 2 at 3.0 mg/kg. Each sub-group further receives as the acute treatment either (1) vehicle, or (2)-(6) the compound of Example 2 at 0.01, 0.03, 0.1, 0.3 or 1.0 mg/kg. All treatments are administered s.c. The results are shown in the table below as mean latency to tail flick in seconds:

| Group | Chronic Treatment | Acute Treatment | Latency (s) |
|---|---|---|---|
| (A) | Vehicle | Vehicle | 1.09 |
| | Vehicle | Ex. 2, 0.01 mg/kg | 1.87 |
| | Vehicle | Ex. 2, 0.03 mg/kg | 2.50 |
| | Vehicle | Ex. 2, 0.1 mg/kg | 5.26 |
| | Vehicle | Ex. 2, 0.3 mg/kg | 8.26 |
| | Vehicle | Ex. 3, 1.0 mg/kg | 9.74 |
| (B) | Ex. 3, 0.3 mg/kg | Vehicle | 0.893 |
| | Ex. 3, 0.3 mg/kg | Ex. 2, 0.01 mg/kg | 1.66 |
| | Ex. 3, 0.3 mg/kg | Ex. 2, 0.03 mg/kg | 1.30 |
| | Ex. 3, 0.3 mg/kg | Ex. 2, 0.1 mg/kg | 2.60 |
| | Ex. 3, 0.3 mg/kg | Ex. 2, 0.3 mg/kg | 3.93 |
| | Ex. 3, 0.3 mg/kg | Ex. 2, 1.0 mg/kg | 5.64 |
| (C) | Ex. 3, 3.0 mg/kg | Vehicle | 1.04 |
| | Ex. 3, 3.0 mg/kg | Ex. 2, 0.01 mg/kg | 1.64 |
| | Ex. 3, 3.0 mg/kg | Ex. 2, 0.03 mg/kg | 1.80 |
| | Ex. 3, 3.0 mg/kg | Ex. 2, 0.1 mg/kg | 3.94 |
| | Ex. 3, 3.0 mg/kg | Ex. 2, 0.3 mg/kg | 4.84 |
| | Ex. 3, 3.0 mg/kg | Ex. 2, 1.0 mg/kg | 7.94 |

It is found that 0.1, 0.3 and 1.0 mg/kg acute treatment with the compound of Example 2 produces a statistically significant dose-dependent analgesic effect compared to in-group acute treatment with vehicle. This is true for each of the chronic groups (A), (B) and (C). As compared to pre-treatment with vehicle, pre-treatment with the compound of Example 2 at 0.3 mg/kg or 3.0 mg/kg generally showed a statistically significant decrease in tail flick latency when the same acute treatment subgroups are compared. These results demonstrate that while some tolerance to the analgesic effect of the compound of Example 2 occurs after 14-days of chronic treatment, the analgesia obtained remains effective despite chronic pre-treatment.

Example 7: CNS Phosphoprotein Profile

A comprehensive molecular phosphorylation study is also carried out to examine the central nervous system (CNS) profile of the compounds of Example 1 and Example 2. The extent of protein phosphorylation for selected key central nervous system proteins is measured in mice nucleus accumbens. Examined proteins include ERK1, ERK2, Glu1, NR2B and TH (tyrosine hydroxylase), and the compounds of Example 1 and 3 were compared to the antipsychotic agents risperidone and haloperidol.

Mice were treated with the compound of Example 1 or 2 at 3 mg/kg, or with haloperidol at 2 mg/kg. Mice were killed 30 minutes to 2 hours post-injection by focused microwave cranial irradiation, which preserves brain phosphoprotein as it exists at the time of death. Nucleus accumbens was then dissected from each mouse brain, sliced and frozen in liquid nitrogen. Samples were further prepared for phosphoprotein analysis via SDS-PAGE electrophoresis followed by phosphoprotein-specific immunoblotting, as described in Zhu H, et al., Brain Res. 2010 Jun. 25; 1342:11-23. Phosphorylation at each site was quantified, normalized to total levels of the protein (non-phosphorylated), and expressed as percent of the level of phosphorylation in vehicle-treated control mice.

The results demonstrate that neither the compound of Example 1 nor of Example 2 has a significant effect on tyrosine hydroxylase phosphorylation at Ser40 at 30 minutes or 60 minutes, in contrast to haloperidol which produces a greater than 400% increase, and risperidone which produces a greater than 500% increase, in TH phosphorylation. This demonstrates that inventive compounds do not disrupt dopamine metabolism.

The results further demonstrate that neither the compound of Example 1 nor of Example 2 has a significant effect on NR2B phosphorylation at Tyr1472 at 30-60 minutes. The compounds produce a slight increase in GluR1 phosphorylation at Ser845, and a slight decrease in ERK2 phosphorylation at Thr183 and Tyr185. Protein phosphorylation at various sites in particular proteins are known to be linked to various activities of the cell such as protein trafficking, ion channel activity, strength of synaptic signaling and changes in gene expression. Phosphorylation the Tyr1472 in the NMDA glutamate receptor has been shown to be essential for the maintenance of neuropathic pain. Phosphorylation of Ser845 of the GluR1 AMPA type glutamate receptor is associated with several aspects of strengthening synaptic transmission and enhanced synaptic localization of the receptor to support long term potentiation associated with cognitive abilities. It has also been reported that phosphorylation of this residue results in an increased probability of channel opening. Phosphorylation of ERK2 kinase, a member of the MAP kinase cascade, at residues T183 and Y185 is required for full activation of this kinase, ERK2 is involved in numerous aspects of cell physiology including cell growth, survival and regulation of transcription. This kinase has been reported to be important in synaptogenesis and cognitive function.

Example 8: Mouse Marble-Burying Study (OCD Model)

The marble burying test is used to measure repetitive and anxiety-related behavior in rodents. It is based on the observation that rats and mice will bury either harmful or harmless objects in their bedding, and it has been used as an animal model to measure the effect of pharmacological interventions in treatment of repetitive behavior disorders, such as OCD.

Mice are first divided up into four treatment groups: (1) vehicle negative control, (2) 0.3 mg/kg compound of Example 2, (3) 1.5 mg/kg compound of Example 2, and (4) 20 mg/kg MPEP (2-methyl-6-(phenylethynyl)pyridine) positive control. MPEP is a selective mGluR5 glutamate receptor antagonist. Mice in groups (2) and (3) are orally administered the compound of Example 2 at the stated dosage in a 0.5% methylcellulose aqueous vehicle 30 minutes prior to the test. Mice in groups (1) are orally administered the vehicle, and mice in group (4) are given an intraperitoneal injection of MPEP just prior to the start of the test.

The test is conducted in rectangular cages with 4-5 cm of wood chip bedding in a room with the window shades lowered and the door closed to minimize distractions. Fifteen clean marbles are evenly spaced on top of the bedding in three rows of five marbles. One mouse is placed in each cage. The mouse and cage is left undisturbed for 30 minutes. At the end of the test, the mouse is removed and the number of marbles buried to at least ⅔ of their depth is counted. The results are shown in the following table:

| Group | Marbles Buried |
|---|---|
| (1) Vehicle | 13.2 |
| (2) 0.3 mg/kg Ex. 2 | 9.3 |
| (3) 1.5 mg/kg Ex. 2 | 4.7 |
| (4) MPEP | 0.2 |

The result demonstrate that compared to the control, there is a statistically significant decrease in marble burying for the mice treated with 0.3 mg/kg of the compound of Example 2 ($p<0.01$) and with 1.5 mg/kg of the compound of Example 2 ($p<0.001$). In addition, there is a clear dose-response relationship evident. The results support the utility of the compound of Example 2 in OCD therapeutic indications.

Example 9: Mu-Opiate Receptor Activity Assays

The compounds of Example 1 and 2 are tested in CHO-K1 cells expressing hOP3 (human mu-opiate receptor μ1 subtype) using an HTRF-based cAMP assay kit (cAMP Dynamic2 Assay Kit, from Cisbio, #62AM4PEB). Frozen cells are thawed in a 37° C. water bath and are resuspended in 10 mL of Ham's F-12 medium containing 10% FBS. Cells are recovered by centrifugation and resuspended in assay buffer (5 nM KCl, 1.25 mM $MgSO_4$, 124 mM NaCl, 25 mM HEPES, 13.3 mM glucose, 1.25 mM $KH_2PO_4$, 1.45 mM $CaCl_2$, 0.5 g/L protease-free BSA, supplemented with 1 mM IBMX). Buprenorphine, a mu-opiate receptor partial agonist, and naloxone, a mu-opiate receptor antagonist, and DAMGO, a synthetic opioid peptide full agonist, are run as controls.

For agonist assays, 12 μL of cell suspension (2500 cells/well) are mixed with 6 μL forskolin (10 μM final assay concentration), and 6 μL of the test compound at increasing concentrations are combined in the wells of a 384-well white plate and the plate is incubated for 30 minutes at room temperature. After addition of lysis buffer and one hour of further incubation, cAMP concentrations are measured according the kit instructions. All assay points are determined in triplicate. Curve fitting is performed using XLfit software (IDBS) and EC values are determined using a 4-parameter logistic fit. The agonist assay measures the ability of the test compound to inhibit forskolin-stimulated cAMP accumulation.

For antagonist assays, 12 μL of cell suspension (2500 cells/well) are mixed with 6 μL of the test compound at increasing concentrations, and combined in the wells of a 384-well white plate and the plate is incubated for 10 minutes at room temperature. 6 μL of a mixture of DAMGO (D-Ala$^2$-N-MePhe$^4$-Gly-ol-enkephelin, 10 nM final assay concentration) and forksolin (10 μM final assay concentration) are added, and the plates are incubated for 30 minutes at room temperature. After addition of lysis buffer, and one hour of further incubation, cAMP concentrations are measured according the kit instructions. All assay points are determined in triplicate. Curve fitting is performed using XLfit software (IDBS) and $IC_{50}$ values are determined using a 4-parameter logistic fit. Apparent dissociation constants ($K_B$) are calculated using the modified Cheng-Prusoff equation. The antagonist assay measures the ability of the test compound to reverse the inhibition of forskolin-induced cAMP accumulation caused by DAMGO.

The results are shown in the Table below. The results demonstrate that the compound of Example 2 is a weak antagonist of the Mu receptor, showing much higher $IC_{50}$ compared to naloxone, and that it is a moderately high affinity, but partial agonist, showing only about 22% agonist activity relative to DAMGO (as compared to about 79% activity for buprenorphine relative to DAMGO). The compound of Example 1 is also shown to have moderately strong partial agonist activity.

| Compound | Antagonist $IC_{50}$ (nM) | Agonist $EC_{50}$ (nM) | $K_B$ (nM) |
|---|---|---|---|
| Naloxone | 5.80 | — | 0.65 |
| DAMGO | — | 1.56 | — |
| Buprenorphine | — | 0.95 | — |
| Cmpd. Ex. 2 | 641 | 64.5 | 71.4 |
| Cmpd Ex. 1 | — | 140 | — |

Buprenorphine is a drug used for chronic pain treatment and for opiate withdrawal, but it suffers from the problem that users can become addicted due to its high partial agonist activity. To offset this, the commercial combination of buprenorphine with naloxone is used (sold as Suboxone). Without being bound by theory, it is believed that the compounds of the present invention, which are weaker partial Mu agonists than buprenorphine, with some moderate antagonistic activity, will allow a patient to be more effectively treated for pain and/or opiate withdrawal with lower risks of addiction.

In additional related study using a recombinant human MOP-beta-arresting signaling pathway, it is found that the Compound of Example 2 does not stimulate beta-arrestin signaling via the MOP receptor at concentrations up to 10 μM, but that it is an antagonist with an $IC_{50}$ of 0.189 μM. In contrast, the full opioid agonist Met-enkephalin stimulates beta-arrestin signaling with an $EC_{50}$ of 0.08 μM.

Example 10: Rat Tolerance/Dependence Study

The compound of Example 2 is assessed during repeated (28 day) daily subcutaneous administration to male Sprague-Dawley rats to monitor drug effects on dosing and to determine if pharmacological tolerance occurs. In addition, behavioral, physical and physiological signs in the rats is monitored following abrupt cessation of repeated dosing to determine whether the compound induces physical dependence on withdrawal. Further, a pharmacokinetic study is performed in parallel with the tolerance and dependence study to determine the plasma drug exposure levels of the compound at the specific doses used in the tolerance and dependence study. Morphine is used as a positive control to ensure validity of the model and as a reference comparator from a similar pharmacological class.

The compound of Example 2 is evaluated at two doses, 0.3 and 3 mg/kg, administered subcutaneously four times per day. Repeated administration is found to produce peak plasma concentrations of 15 to 38 ng/mL (average, n=3) for 0.3 mg/kg dosing, and 70 to 90 ng/mL (average, n=3) for 3 mg/kg dosing. Peak concentration is reached at 30 minutes to 1.5 hours post-administration with comparable results obtained on the 1st, 14th and 28th day of administration.

At both doses of Example 2, it is found that there is no significant effect on animal body weight, food and water intake or body temperature during either the on-dose or withdrawal phase. The predominant behavioral and physical effects caused by repeated administration at 0.3 mg/kg is found to be hunched posture, Straub tail and piloerection during the dosing phase. At the higher dose, the main behavioral and physical signs observed are hunched posture, subdued behavior, Straub tail, tail rattle and piloerection.

A similar profile of behavioral and physical signs is observed following abrupt cessation of the compound on Day 28 of the study. While rearing and increased body tone were not observed during the on-dose phase for at 0.3 mg/kg, it is found to be significantly increased during the withdrawal phase. At the higher dose, mild rearing is observed during the on-dose phase, but during the withdrawal phase, rearing is more pronounced and increased body tone is observed.

As a positive control, morphine is doses at 30 mg/kg orally twice per day. This dosing regimen, as expected, is observed to be associated with changes in body weight, food and water intake, rectal temperature and clinical signs consistent with the development of tolerance and withdrawal-induced dependence. Body weight was significantly increased compared with the vehicle-treated control group on Days 2 and 3, while it was significantly decreased from Day 5. Morphine decreased food intake significantly on Days 1-9. Thereafter food intake is generally observed to be lower than for the control group, but was not significantly different from controls on Days 9, 13, 14, 16, 18, 21, 22 and Day 25. These effects on body weight and food intake demonstrate tolerance to the effect of morphine.

Water intake of the morphine-treated group is also found to be significantly lower than the control group on 25 out of 28 days during the on-dose phase. Body temperature is also generally lower than the control group during the on-dose phase, significantly so on Days 20, 21 and 27. The predominant behavioral effects induced by morphine during the on-dose phase are observed to be Straub tail, jumping, digging, increased body tone, increased locomotor activity, explosive movements and exopthalmus.

Furthermore, withdrawal of morphine administration on Day 28 is observed to result in an initial further decrease in food intake followed by rebound hyperphagia, with significantly increased food intake on Day 33 versus the control group. Food intake returns to control levels by Day 35. Similarly, rats which had previously received morphine also are observed to have an initial reduction in water intake on Day 29, followed by rebound hyperdipsia (water consumption returns to control levels by Day 31). In addition, statistically significant decreases in rectal body temperature are observed during dosing, but body temperature returns to control levels during the withdrawal phase.

Moreover, new behavioral and physical signs are observed during the withdrawal phase from morphine, and this demonstrates the presence of dependence. These signs include piloerection, ataxia/rolling gait, wet dog shakes and pinched abdomen. Other abnormal behaviors observed during the on-dose phase gradually disappear during the withdrawal phase. By Day 35, rearing was the only behavior or physical sign observed with high incidence in the rats that had previously received morphine.

Thus, repeated morphine administration is shown to produce clear signs of tolerance and dependence in this study, with changes in body weight, food and water intake, rectal temperature and clinical signs consistent with the development of tolerance and withdrawal induced dependence. This demonstrates the validity of the study method in detecting physiological alterations during administration and cessation of dosing.

In contrast, repeated administration of the Compound of Example 2, at both 0.3 and 3 mg/kg four times, does not produce tolerance during subcutaneous dosing for 28 days. Furthermore, on withdrawal, a similar but decreasing profile of behavioral and physical signs is observed at the highest dose, which is not considered to be of clinical significance. Thus, overall the Compound of Example 2 was found not to produce a syndrome of physical dependence upon cessation of dosing.

Example 11: Oxycodone-Dependent Withdrawal Study in Mice

Oxycodone is administered to male C57BL/6J mice for 8 days at an increasing dose regimen of 9, 17.8, 23.7, and 33 mg/kg b.i.d. (7 hours between injections) on days 1-2, 3-4, 5-6 and 7-8 respectively. On the morning of the ninth day, the mice are administered the compound of Example 3 at either 0.3, 1 or 3 mg/kg subcutaneous. This is followed 30 minute later by either an injection of vehicle or with an injection of 3 mg/kg of naloxone. Another cohort of mice serve as negative controls, and instead of oxycodone, these mice are administered saline on days 1 to 8. On day 9, these mice are administered either vehicle (followed by naloxone, as above) or the compound of Example 2 at 3 mg/kg, s.c. (followed by naloxone, as above).

On day 9, immediately after the injection of naloxone (or vehicle), the mice are individually placed in clear, plastic cages and are observed continuously for thirty minutes. The mice are monitored for common somatic signs of opiate withdrawal, including jumping, wet dog shakes, paw tremors, backing, ptosis, and diarrhea. All such behaviors are recorded as new incidences when separated by at least one second or when interrupted by normal behavior. Animal body weights are also recorded immediately before and 30 minutes after the naloxone (or vehicle) injections. Data is analyzed with ANOVA followed by the Tukey test for multiple comparisons, when appropriate. Significant level is established at $p<0.05$.

The results are shown in the Table below:

| Dosing: (1) on days 1-8, (2) on day 9, followed by (3) 30 minutes later | Total Number of Signs | Paw Tremors | Jumps | Body Weight Loss |
|---|---|---|---|---|
| (1) Saline; (2) Vehicle, (3) Naloxone | 2.2 | 0.87 | 0 | 0.5% |
| (1) Saline; (2) Compound 3.0 mg/kg, (3) Naloxone | 5.3 | 0.12 | 0 | 0.4% |
| (1) Oxycodone; (2) Compound 3.0 mg/kg, (3) Vehicle | 155.1 | 73.6 | 63.2 | 7.8% |
| (1) Oxycodone; (2) Compound 0.3 mg/kg, (3) Naloxone 3 mg/kg | 77.5 | 19.6 | 40.6 | 7.5% |
| (1) Oxycodone; (2) Compound 1.0 mg/kg, (3) Naloxone 3 mg/kg | 62.5 | 14.8 | 34.8 | 6.0% |
| (1) Oxycodone; (2) Compound 3.0 mg/kg, (3) Naloxone 3 mg/kg | 39.5 | 0.5 | 26.6 | 4.0% |

Total number of signs includes paw tremors, jumps, and wet dog shakes. In oxycodone-treated mice, it is found that naloxone elicits a significant number of total signs, paw tremors, jumps and body weight change ($p \leq 0.0001$ for each). At all doses tested, the compound of Example 2 produces a significant decrease in total number of signs and paw tremors. In addition, at 3.0 mg/kg, the compound also produces a significant decrease in jumps and attenuated body weight loss.

These results demonstrate that the compound of Example 2 dose-dependently reduces the signs and symptoms of opiate withdrawal after the sudden cessation of opiate administration in opiate-dependent rats.

Example 12: Formalin Paw Test (Inflammatory Pain Model)

Sub-plantar administration of chemical irritants, such as formalin, causes immediate pain and discomfort in mice, followed by inflammation. Subcutaneous injection of 2.5% formalin solution (37 wt % aqueous formaldehyde, diluted with saline) into the hind paw results in a biphasic response: an acute pain response and a delayed inflammatory response. This animal model thus provides information on both acute pain and sub-acute/tonic pain in the same animal.

C57 mice are first habituated in an observation chamber. 30 minutes prior to formalin challenge, mice are administered either vehicle injected subcutaneously, 5 mg/kg of morphine (in saline) injected subcutaneously, or the compound of Example 2 (in 45% w/v aqueous cyclodextrin) injected subcutaneously at either 0.3, 1.0 or 3.0 mg/kg. In addition, another set of mice are treated with the control vehicle or the compound of Example 2 at 3.0 mg/kg, via oral administration, rather than subcutaneous injection.

The mice are then given a subcutaneous injection into the plantar surface of the left hind paw of 20 μL of 2.5% formalin solution. Over the next 40 minutes, the total time spent licking or biting the treated hind-paw is recorded. The first 10 minutes represent the acute nociceptive response, while the latter 30 minutes represents the delayed inflammatory response. At one minter intervals, each animal's behavior is assessed using "Mean Behavioral Rating," which is scored on a scale of 0 to 4:

0: no response, animal sleeping
  1: animal walking lightly on treated paw, e.g., on tip-toe
  2: animal lifting treated paw
  3: animal shaking treated paw
  4: animal licking or biting treated paw Data are analyzed by ANOVA followed by post-hoc comparisons with Fisher tests, where appropriate. Significance is established at $p<0.05$.

The results are shown in the Table below.

| | Mean Behavior Rating (0-4) | | | | Mean Licking Time (min) | | | |
|---|---|---|---|---|---|---|---|---|
| | 0-10 Min | 11-40 min | 0-6 min | 16-40 min | 0-10 min | 11-40 min | 0-6 min | 16-40 min |
| Vehicle (SC) | 1.4 | 1.4 | 2.1 | 1.5 | 34 | 75 | 32 | 76 |
| Vehicle (PO) | 1.2 | 0.9 | 1.9 | 1.0 | 29 | 50 | 33 | 40 |
| Morphine | 1.1 | 0.2 | 1.7 | 0.2 | 11 | 0 | 11 | 0 |
| Cmpd, SC 0.3 mg/kg | 1.5 | 1.0 | 2.3 | 1.2 | 31 | 68 | 34 | 70 |
| Cmpd, SC 1.0 mg/kg | 1.3 | 1.0 | 1.9 | 1.1 | 26 | 60 | 26 | 65 |
| Cmpd, SC 3.0 mg/kg | 0.8 | 0.1 | 1.3 | 0.1 | 14 | 36 | 11 | 36 |
| Cmpd, PO 3.0 mg/kg | 0.9 | 0.8 | 1.5 | 0.9 | 11 | 3 | 9 | 3 |

The results demonstrate a significant treatment effect during both the early phase (0-10 min) and late phase (11-40 min) response periods. Post-hoc comparisons show that, compared to vehicle treatment, subcutaneous injection of morphine or the compound of Example 2 (at 3 mg/kg) significantly attenuates the pain behavior rating induced by formalin injection, as well as significantly reducing licking time. Post-hoc comparisons also show that subcutaneous injection of morphine or the compound of Example 2 (at 3 mg/kg), as well as the compound of Example 2 orally (at 3 mg/kg), significantly reduces time spent licking. While the mean pain behavior rating was also reduced using 1.0 mg/kg of compound subcutaneous and at 3.0 mg/kg oral, these effects were not statistically significant in this study. Licking time was similarly reduced using 1.0 mg/kg of the compound of Example 2 subcutaneously, but the result was not statistically significant in this study. It was also found that no mice in the study underwent significant changes in body weight in any of the study groups.

Example 13: Self Administration in Heroin-Maintained Rats

A study is performed to determine whether heroin-addicted rats self-administer the compound of Example 2, and it is found that they do not, further underscoring the non-addictive nature of the compounds of the present disclosure.

The study is performed in three stages. In the first stage, rats are first trained to press a lever for food, and they are then provided with an in-dwelling intravenous jugular catheter and trained to self-administer heroin. In response to a cue (the lighting of a light in the cage), three presses of the lever by the animal results in a single heroin injection via the catheter. The heroin is provided at an initial dose of 0.05 mg/kg/injection, and later increased to 0.015 mg/kg/injection. This trained response is then extinguished by replacing the heroin supply with saline. In the second phase, the saline solution is replaced by a solution of the compound of Example 2, at one of four doses: 0.0003 mg/kg/injection, 0.001 mg/kg/injection, 0.003 mg/kg/injection, and 0.010 mg/kg/injection. Each individual rat is provided with either one or two different doses of the compound in rising fashion. This response is then extinguished with saline injections, followed by the third phase, which repeats the use of heroin at 0.015 mg/kg/injection. The purpose of the third phase is to demonstrate that the rats still show addictive behavior to heroin at the end of the study. The study results are shown in the table below:

| Treatment | Animals (n) | Mean Lever presses |
|---|---|---|
| Saline Extinction 1 | 21 | 4.08 |
| Heroin Acquisition (0.015 mg/kg/inj) | 21 | 19.38* |
| Cmpd. Ex. 2 at 0.0003 mg/kg/inj | 8 | 3.17** |
| Cmpd. Ex. 2 at 0.0003 mg/kg/inj | 8 | 3.29** |
| Cmpd. Ex. 2 at 0.0003 mg/kg/inj | 8 | 3.99** |
| Cmpd. Ex. 2 at 0.0003 mg/kg/inj | 8 | 4.87** |
| Saline Extinction 2 | 19 | 3.60** |
| Heroin Reinstatement (0.015 mg/kg/inj) | 19 | 17.08** |

*$P < 0.001$ for heroin acquisition vs. saline extinction 1 (multiple t test);
**$P < 0.001$ for Cmpd of Ex. 2 vs. heroin acquisition (Dunnett's test);
$P > 0.7$ for all comparisons between Cmpd. of Ex. 2 and saline extinction 1 (William's test)

The results demonstrate that there is a statistically significant increase in lever pressing by the rats when being administered heroin, but that there was no significant difference when being administered saline or the compound of Example 2. Thus, the results suggest that rats do not become addicted to the compound of Example 2.

Example 14: Animal Pharmacokinetic Data

Using standard procedures, the pharmacokinetic profile of the compound of Example 2 is studied in several animals.

Example 14a: Rat PK Studies

In a first study, rats are administered the compound of Example 2 either by intravenous bolus (IV) at 1 mg/kg in 45% Trapposol vehicle, or orally (PO) at 10 mg/kg in 0.5% CMC vehicle (N=3 each group). In a second study, rats are administered the compound of Example 2 at 10 mg/kg PO or 3 mg/kg subcutaneously (SC), each in 45% Trapposol vehicle (N=6 for each group). Plasma concentrations of the drug are measured at time points from 0 to 48 hours post dose. Representative results are tabulated below (* indicates plasma concentration below measurable level of quantitation):

|  | Study One | | Study Two | |
|---|---|---|---|---|
|  | IV (1 mg/kg) | PO (10 mg/kg) | PO (10 mg/kg) | SC (3 mg/kg) |
| 30 min (ng/mL) | 99.0 | 30.7 | 54.9 | 134.4 |
| 1 hour (ng/mL) | 47.3 | 37.2 | 60.6 | 140.9 |
| 6 hours (ng/mL) | 1.1 | 9.4 | 21.0 | 18.2 |
| 24 hours (ng/mL) | * | 0.1 | 0.4 | 1.9 |
| 48 hours (ng/mL) | * | * | ND | ND |
| Cmax (ng/mL) | 314.8 | 37.2 | 60.6 | 140.9 |
| AUC (ng-hr/mL) | 182 | 215 | 409 | 676 |
| Bioavailability | 100% | 12% | 22% | 123% |
| t-½ (hr) |  |  | 3.1 | 9.5 |

Example 14b: Mice PK Studies

A similar study in mice is performed using 10 mg/kg PO administration of the compound of Example 2, and the following results are obtained: Tmax=0.25 hours; Cmax=279 ng/mL; AUC (0-4 h)=759 ng-hr/mL; blood-plasma ratio (0.25-4 h) ranges from 3.7 to 6.6. The study is also conducted at a dose of 0.1 mg/kg SC. Representative results are shown in the table below:

| | Study: | | | |
|---|---|---|---|---|
| | PO, 10 mg/kg (0.5% CMC veh) | | SC, 0.1 mg/kg (45% Trapposol veh) | |
| Time (hr) | Plasma (ng/mL) | Brain (ng/g) | Plasma (ng/mL) | Brain (ng/g) |
| 0.25 | 279 | 1288 | 27.5 | 57.1 |
| 0.5 | 179 | 1180 | 31.1 | 71.9 |
| 1 | 258 | 989 | 29.2 | 78.5 |
| 2 | 153 | 699 | 14.6 | 38.7 |
| 4 | 199 | 734 | 4.7 | 32.6 |
| Tmax (hr) | 0.25 | 0.25 | 0.5 | 1.0 |
| Cmax (ng/mL) | 279 | 1288 | 31.1 | 78.5 |
| AUC0-4 h (ng-hr/mL) | 759 | 2491 | 67 | 191 |
| B/P Ratio | 3.3 | | 2.8 | |

Together these results show that the compound of Example 2 is well-absorbed and distributed to the brain and tissues and is retained with a reasonably long half-life to enable once-daily administration of therapeutic doses.

Example 15: Gastrointestinal Function

The effect of the compound of Example 2 on gastrointestinal motility in rats is examined by monitoring the rate of intestinal transit of an activated charcoal bolus. Rats were treated with either (1) aqueous carboxymethyl cellulose vehicle, (2) morphine (5 mg/kg, SC), or (3) the compound of Example 3 (at 0.3, 1.0 or 3.0 mg/kg, SC) 30 minutes prior to an oral bolus of 15% aqueous activated charcoal. The measured outcome is motility ratio, calculated as the distance traveled by the charcoal as a fraction of the full length of the animal's intestine. The results are shown in the table below:

| Group (n = 10 each) | Treatment | Motility Ratio |
|---|---|---|
| 1 | Vehicle | 0.55 |
| 2 | Cmpd. Ex. 2, 0.3 mg/kg | 0.50 |
| 3 | Cmpd. Ex. 2, 1 mg/kg | 0.55 |
| 4 | Cmpd. Ex. 2, 3 mg/kg | 0.50 |
| 5 | Morphine, 5 mg/kg | 0.27 |

These results show that the compound of Example 2 has no significant effect on gastrointestinal motility at a dose up to 3 mg/kg. In contrast, and as expected, morphine results in approximately a 50% reduction in gastric motility.

In a further experiment, rats were pre-treated 60 minutes prior to the charcoal bolus with either vehicle, morphine (5 mg/kg), or the compound of Example 2 (3 mg/kg), each SC, followed by treatment with either morphine (5 mg/kg), morphine plus compound of Ex. 2 (0.3 mg/kg or 3 mg/kg), or compound of Ex. 2 (3 mg/kg) alone. The results are shown in the table below. For groups 2 and 3, morphine was injected first, followed immediately by the injection of the compound of Example 2:

| Group (n = 8 each) | Pre-Treatment | Treatment | Motility Ratio |
|---|---|---|---|
| 1 | Vehicle | Morphine, 5 mg/kg | 0.21 |
| 2 | None | Morphine, 5 mg/kg + Cmpd. Ex. 2, 0.3 mg/kg | 0.26 |
| 3 | None | Morphine, 5 mg/kg + Cmpd. Ex. 2, 3 mg/kg | 0.32 |
| 4 | Morphine, 5 mg/kg | Cmpd. Ex. 2, 3 mg/kg | 0.41 |
| 5 | Cmpd. Ex. 2, 3 mg/kg | Morphine, 5 mg/kg | 0.30 |

The results show that the compound of Example 2 reverses the inhibition of gastrointestinal motility caused by morphine when given either concurrently or sequentially prior to morphine, with the blockade of morphine's effect stronger when pre-treatment is used.

Without being bound by theory, it is believed that these differences result from the compound of Example 2 acting as biased MOP ligands and its failure to activate beta-arrestin signaling pathways downstream, which pathways have been shown to mediate opiate-linked side effects, including constipation and respiratory depression.

Example 16: Pulmonary Function

The effect of the compound of Example 2 on pulmonary function in rats is examined by monitoring respiratory rate, tidal volume and minute volume in rats following the subcutaneous administration of the compound of Example 2 at 0.3, 1.0 and 3.0 mg/kg, compared to vehicle control. Measurements are taken at 0, 15, 60, 120, and 240 minutes following administration of the compound. It is found that there are no significant differences between the vehicle and any of the test groups at any time point. Results are shown below for 60 minutes, which is typical of the results obtained:

|  | RR (breaths/min) | TV (mL) | MV (mL/min) |
|---|---|---|---|
| Vehicle | 188 | 1.10 | 195 |
| Cmpd. Ex. 2, 0.3 mg/kg | 181 | 1.06 | 181 |
| Cmpd. Ex. 2, 1.0 mg/kg | 203 | 0.86 | 169 |
| Cmpd. Ex. 2, 3.0 mg/kg | 190 | 0.97 | 179 |

Example 17: Synthesis of 1-(Acyloxy)alkyl Derivatives

A series of compounds according to Formula I, wherein Z is —O— and wherein $R^5$ is —C($R^6$)($R^7$)—O—C(O)—$R^8$, and wherein $R^6$, $R^7$ and $R^8$ are as follows, are prepared starting from the precursor Compound 14a:

| Compound | $R^6$ | $R^7$ | $R^8$ |
|---|---|---|---|
| 17b | H | H | $CH_3(CH_2)_{10}$ |
| 17c | H | H | $CH_3(CH_2)_{14}$ |

Each compound is prepared by reacting Compound 17a, (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one, with the appropriate chloromethyl alkylate 17x ($R^8CO_2C(R^6)(R^7)Cl$). The necessary chloromethyl alkylates are each prepared from the corresponding acid chloride, $R^8COCl$.

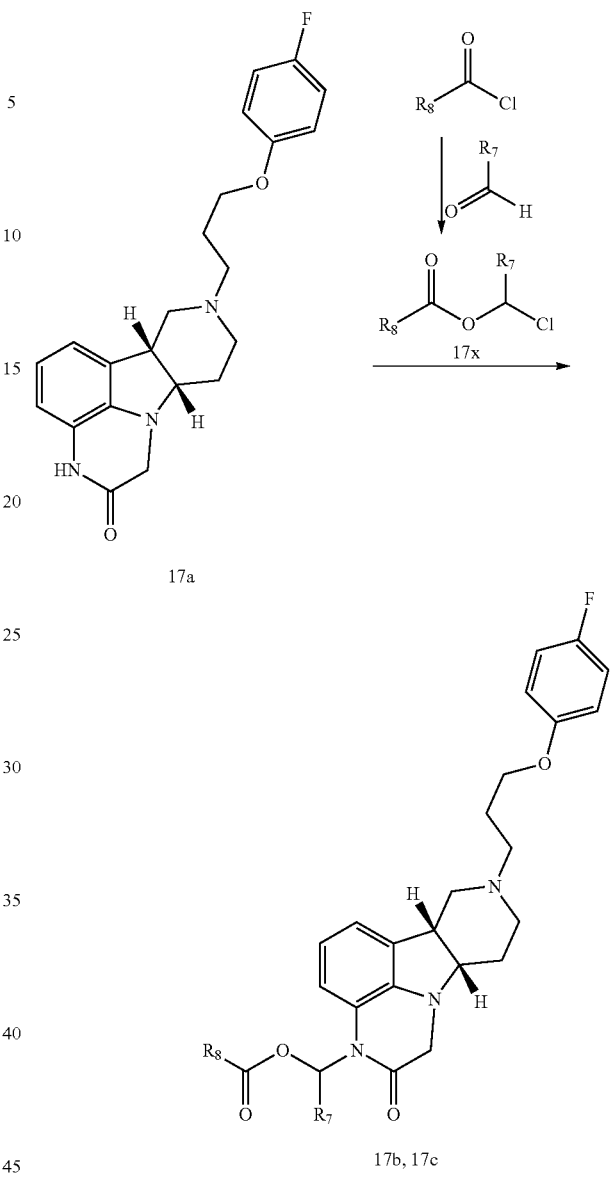

For example, chloromethyl dodecanoate ($CH_3(CH_2)_{10}$—C(O)O—$CH_2Cl$) is prepared as follows. To a stirred suspension of zinc(II) chloride (294 mg, 2.16 mmol) and paraformaldehyde (842 mg, 28.08 mmol) in anhydrous acetonitrile (4 mL) at 0° C. is added lauryl chloride (5.0 mL, 21.6 mmol) dropwise under argon. The suspension is stirred at 0° C. for 10 min and at room temperature for 10 min, and then is heated up to 70° C. for 24 h. The reaction mixture is then cooled to room temperature and poured into dichloromethane (100 mL). The resulting suspension is filtered under vacuum and washed with dichloromethane (2×10 mL). To the combined filtrate is added saturated sodium bicarbonate (100 mL) and the mixture is stirred at room temperature for 1.5 h. The dichloromethane phase is separated and washed with saturated sodium bicarbonate (2×60 mL), and evaporated to dryness under reduced pressure. The resulting residue is further dried under high vacuum to give chloromethyl dodecanoate as a light orange oil (4.523 g, 84% yield). This crude product is directly used for the next reaction without further purification. Chloromethyl dodecanoate is used for the preparation of compound 17b. For the preparation of compound 17c, chloromethyl palmitate is used, which is prepared from palmitoyl chloride and paraformaldehyde. Analogous compounds 17x may be made analogously using other acid chlorides, such as octanoyl chloride or stearyl chloride along other aldehydes, such as acetaldehyde, propionaldehyde or isobutyraldehyde.

Compound 17b. A suspension of potassium iodide (131 mg, 0.786 mmol), potassium carbonate (181 mg, 1.31 mmol), N,N-diisopropylethylamine (137 µL, 0.786 mmol), N,N-dimethylpyridin-4-amine (64 mg, 0.524 mmol), chloromethyl dodecanoate (522 mg, 2.10 mmol), and 17a (212 mg, 0.556 mmol) in anhydrous DMF (1.5 mL) is bubbled with argon for 5 min. The resulting suspension is heated up to 125° C. by microwave for 5 h, and the solvent is removed under reduced pressure. The obtained crude product is purified by silica-gel column chromatography using a gradient of 0-100% ethyl acetate in hexane as eluent to afford ((6bR,10aS)-8-(3-(4-fluorophenoxy)propyl)-2-oxo-6b,7,8,9,10,10a-hexahydro-1H-pyrido[3',4':4,5]pyrrolo[1,2,3-de]quinoxalin-3(2H)-yl)methyl dodecanoate (17b) as a light orange solid (150 mg, 45% yield). MS (ESI) m/z 594.4089 [M+H]+. $^1$H NMR (500 MHz, Chloroform-d) δ 6.96 (dd, J=9.1, 8.2 Hz, 2H), 6.90 (s, 1H), 6.82 (d, J=7.0 Hz, 4H), 6.16 (d, J=10.5 Hz, 1H), 5.70 (d, J=10.5 Hz, 1H), 4.05 (d, J=14.5 Hz, 1H), 3.99 (d, J=6.6 Hz, 2H), 3.42 (d, J=14.4 Hz, 1H), 3.38-3.25 (m, 1H), 2.91 (d, J=28.2 Hz, 1H), 2.74 (s, 1H), 2.50 (s, 2H), 2.34 (t, J=7.5 Hz, 2H), 2.28 (t, J=7.9 Hz, 1H), 1.96 (s, 3H), 1.86 (s, 1H), 1.70-1.59 (m, 2H), 1.54 (s, 1H), 1.35-1.16 (m, 17H), 0.88 (t, J=6.9 Hz, 3H).

Compounds 17c is prepared in analogous fashion using the appropriate halides 14x. For example, Compound 17c is obtained using chloromethyl palmitate. MS (ESI) m/z 650.4348 [M+H]+. 1H NMR (500 MHz, Chloroform-d) δ 6.96 (dd, J=9.1, 8.2 Hz, 2H), 6.89 (dd, J=5.5, 2.8 Hz, 1H), 6.86-6.78 (m, 4H), 6.16 (d, J=10.5 Hz, 1H), 5.70 (d, J=10.5 Hz, 1H), 4.05 (d, J=14.5 Hz, 1H), 3.97 (t, J=6.3 Hz, 2H), 3.41 (d, J=14.5 Hz, 1H), 3.32 (d, J=5.6 Hz, 2H), 2.97-2.89 (m, 1H), 2.74 (d, J=11.3 Hz, 1H), 2.57-2.42 (m, 2H), 2.34 (t, J=7.5 Hz, 2H), 2.30-2.20 (m, 1H), 2.00-1.91 (m, 3H), 1.85 (t, J=11.0 Hz, 1H), 1.62 (p, J=7.4 Hz, 2H), 1.53 (s, 2H), 1.35-1.18 (m, 23H), 0.88 (t, J=6.9 Hz, 3H).

Example 18: Synthesis of Alkoxycarbonyl (Carbamate) Derivatives

A series of compounds according to Formula I, wherein Z is —O— and wherein $R^5$ is —C(O)—O—C($R^a$)($R^b$)($R^c$), and wherein $R^a$, $R^b$ and $R^c$ are as follows, is prepared:

| Compound | $R^a$ | $R^b$ | $R^c$ |
|---|---|---|---|
| 18a | H | H | $CH_3(CH_2)_9$ |
| 18b | H | H | $CH_3(CH_2)_{13}$ |

Each compound is prepared by reacting Compound 17a with the appropriate alkoxycarbonyl chloride, $R^cCH_2O(CO)Cl$:

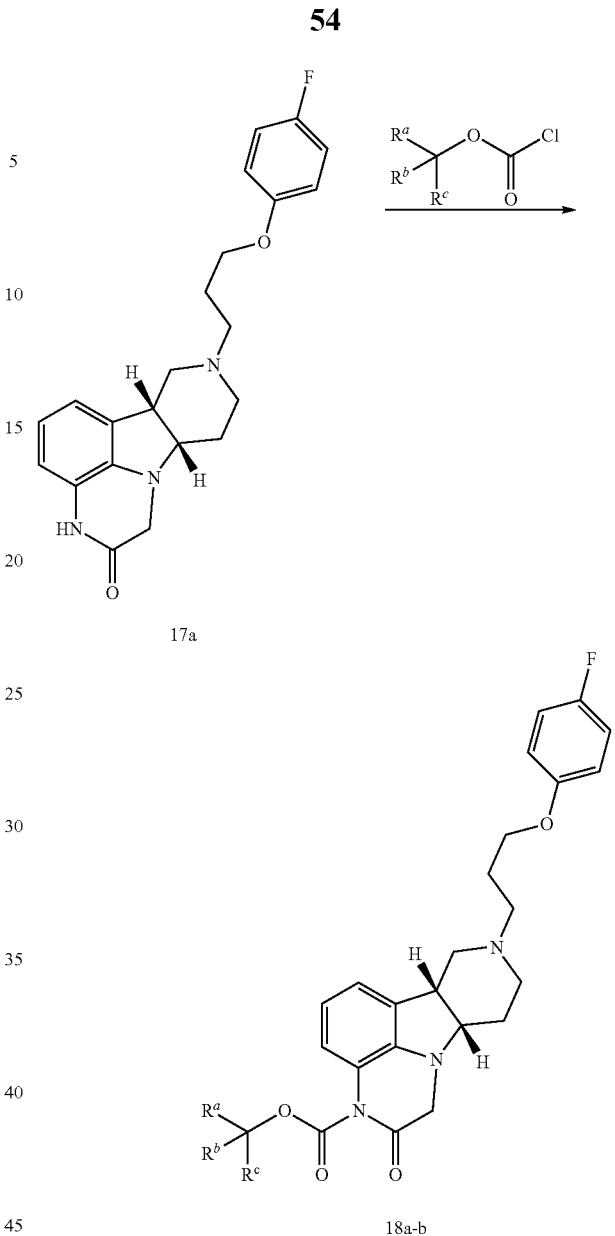

Compound 18b. A mixture of N,N-diisopropylethylamine (219 µL, 1.572 mmol), N,N-dimethyl-pyridin-4-amine (64 mg, 0.524 mmol), hexadecyloxycarbonyl chloride (320 mg, 1.05 mmol), and 17a (200 mg, 0.524 mmol) in anhydrous DMF (3 mL) is bubbled with argon for 5 min. The mixture is stirred at room temperature for 5 h, and the solvent is removed under reduced pressure. The obtained residue is purified by silica-gel column chromatography using a gradient of 0-100% ethyl acetate in hexane as eluent to give the title compound as a light orange solid (197 mg, 58% yield. MS (ESI) m/z 650.4970 [M+H]+. 1H NMR (500 MHz, Chloroform-d) δ 7.04 (d, J=8.2 Hz, 1H), 6.96 (dd, J=9.2, 8.2 Hz, 2H), 6.91 (d, J=7.3 Hz, 1H), 6.86-6.76 (m, 3H), 4.40 (t, J=6.7 Hz, 2H), 4.04-3.94 (m, 3H), 3.35 (d, J=14.1 Hz, 2H), 3.26 (d, J=5.3 Hz, 1H), 2.92 (s, 1H), 2.74 (s, 1H), 2.50 (s, 2H), 2.24 (d, J=14.8 Hz, 1H), 2.00-1.86 (m, 4H), 1.83-1.74 (m, 2H), 1.48-1.38 (m, 2H), 1.26 (s, 25H), 0.88 (t, J=6.9 Hz, 3H).

Compound 18a. Compound 18a is obtained in analogous fashion using dodecanoxycarbonyl chloride. MS (ESI) m/z 594.4180 [M+H]+. 1H NMR (500 MHz, Chloroform-d) δ 7.06 (dd, J=8.2, 0.9 Hz, 1H), 6.99-6.91 (m, 3H), 6.86-6.76 (m, 3H), 4.41 (t, J=6.7 Hz, 2H), 4.00-3.96 (m, 2H), 3.53 (s, 1H), 3.36 (d, J=14.0 Hz, 1H), 3.29 (d, J=4.0 Hz, 1H), 3.12 (s, 1H), 2.96 (s, 1H), 2.70 (d, J=11.9 Hz, 2H), 2.48 (s, 1H), 2.19 (s, 1H), 2.13-2.02 (m, 2H), 2.03-1.94 (m, 1H), 1.83-1.72 (m, 2H), 1.47-1.39 (m, 2H), 1.27 (d, J=6.3 Hz, 18H), 0.88 (t, J=6.9 Hz, 3H).

Example 19: Pharmacokinetic Analysis of the Compounds 17b and 18a

Rat PK studies are performed substantially according to the same protocol as used in Example 14a. Rats are dosed subcutaneously with the Compound of Example 2, the Compound 17b or the Compound 18a, at 30 mg/kg, in a vehicle consisting of 3% CMC, 0.1% Tween 20 in normal saline (0.9% NaCl) (N=4 for each groups). Plasma samples are taken at 2, 5, 15 and 30 minutes, and at 1, 2, 6, 8, 12, 24, 48, 72, 96, 120, 144, 168, 240, 336, 504 and 720 hours. Samples are analyzed for the concentration of the administered compound (Ex. 2, Cmpd. 17b or 18a), as well as for the compound of Example 2 (which is the hydrolytic metabolite of the Compounds 17b and 18a). Representative results are shown in the table below (* indicates an analyte level below the measurable level of quantitation):

|  | Administered: | | | | |
| --- | --- | --- | --- | --- | --- |
|  | Cmpd Ex. 2 | Cmpd 17b | | Cmpd 18a | |
|  | | Analyte: | | | |
|  | Cmpd Ex. 2 (ng/mL) | Cmpd 17b (ng/mL) | Cmpd Ex. 2 (ng/mL) | Cmpd 18a (ng/mL) | Cmpd Ex. 2 (ng/mL) |
| 30 minutes | 9.2 | 1.6 | 7.7 | 1.8 | 1.0 |
| 1 hour | 13.2 | 1.4 | 9.2 | 1.7 | 1.0 |
| 6 hours | 10.9 | 0.7 | 7.5 | 1.3 | 0.5 |
| 24 hours | 5.6 | 0.8 | 2.7 | 0.9 | 0.1 |
| 72 hours | 3.9 | * | 1.7 | 0.2 | 0.2 |
| 144 hours | 6.7 | * | 5.0 | * | 0.2 |
| 336 hours | 8.0 | * | 4.3 | * | * |
| 720 hours | 2.3 | * | 0.6 | ND | ND |
| Tmax (hr) | 2 | 0.25 | 1 | 0.5 | 0.03 |
| Cmax (ng/mL) | 14.5 | 1.7 | 9.2 | 1.8 | 1.5 |
| AUCobs (ng-hr/mL) | 5416 | 18 | 2332 | 56 | 29 |

These results demonstrate that the compounds of the present disclosure undergo effective metabolic hydrolysis to yield therapeutic plasma concentrations of the active drug moiety, the compound of Example 2. Furthermore, the results show that these compounds undergo a gradual in vivo hydrolysis which significantly prolongs the time frame over which measurable plasma concentrations of the compound of Example 2 are found (by comparison to the results shown in Example 14a). For example, when the compound of Example 2 is administered to rats subcutaneously at the therapeutically effective dose of 3 mg/kg, the plasma concentration of the drug is seen to fall to near baseline levels at 24 hours post-dosing (see Example 14a). In contrast, when the pro-drug Compound 17b is administered at the dose of 30 mg/kg, significant plasma concentrations of the compound of Example 2 are obtained up to 336 hours later.

The invention claimed is:

1. A pharmaceutical composition comprising a compound of a Formula I:

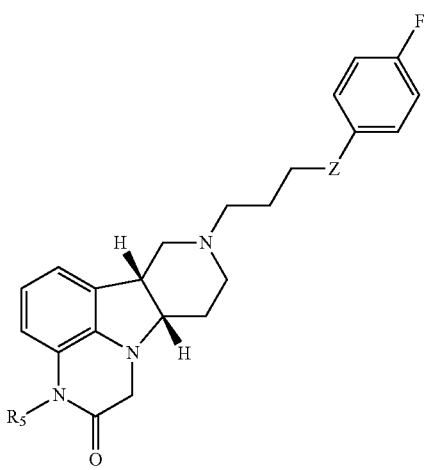

Formula I wherein:

$R^5$ is —C(O)—O—C($R^a$)($R^b$)($R^c$), —C(O)—O—CH$_2$—O—C($R^a$)($R^b$)($R^c$) or —C($R^6$)($R^7$)—O—C(O)—$R^8$;

Z is O, or —C(O)—;

$R^8$ is —C($R^a$)($R^b$)($R^c$), —O—C($R^a$)($R^b$)($R^c$), or —N($R^d$)($R^e$);

$R^a$, $R^b$ and $R^c$ are each independently selected from H and $C_{1-24}$alkyl;

$R^d$ and $R^e$ are each independently selected from H and $C_{1-24}$alkyl;

$R^6$ and $R^7$ are each independently selected from H, $C_{1-6}$alkyl, carboxy and $C_{1-6}$alkoxycarbonyl;

in free or pharmaceutically acceptable salt form;

or a compound of a Formula II:

Formula II wherein:

Z is O, or —C(O)—;

$R^1$, $R^2$, $R^3$ and $R^4$ are each independently selected from H and $C_{1-6}$alkyl;

n is an integer from 1 to 23;

in free or pharmaceutically acceptable salt form;

in admixture with a pharmaceutically acceptable diluent or carrier;

wherein the composition is formulated as a long acting injectable for intramuscular or subcutaneous injection.

2. The pharmaceutical composition comprising the compound of Formula I according to claim 1, wherein Z is O.

3. The pharmaceutical composition comprising the compound of Formula I according to claim 1, wherein Z is —C(O).

4. The pharmaceutical composition comprising the compound of Formula I according to claim 1, wherein $R^5$ is —C(O)—O—C($R^a$)($R^b$)($R^c$).

5. The pharmaceutical composition comprising the compound of Formula I according to claim 1, wherein $R^5$ is —C(O)—O—$CH_2$—O—C($R^a$)($R^b$)($R^c$).

6. The pharmaceutical composition comprising the compound of Formula I according to claim 1, wherein $R^5$ is —C($R^6$)($R^7$)—O—C(O)—$R^8$, and $R^8$ is —C($R^a$)($R^b$)($R^c$).

7. The pharmaceutical composition comprising the compound of Formula I according to claim 1, wherein $R^5$ is —C($R^6$)($R^7$)—O—C(O)—$R^8$, and $R^8$ is —O—C($R^a$)($R^b$)($R^c$).

8. The pharmaceutical composition comprising the compound of Formula I according to claim 1, wherein $R^5$ is —C($R^6$)($R^7$)—O—C(O)—$R^8$, and $R^8$ is —N($R^d$)($R^e$).

9. The pharmaceutical composition comprising the compound of a Formula II according to claim 1:

Formula II wherein:

Z is O, or —C(O)—;

$R^1$, $R^2$, $R^3$ and $R^4$ are each independently selected from H and $C_{1-6}$alkyl;

n is an integer from 1 to 23;

in free or pharmaceutically acceptable salt form.

10. The pharmaceutical composition according to claim 1, wherein the composition comprises the compound in the form of a pharmaceutically acceptable salt.

11. The pharmaceutical composition according to claim 1, wherein the composition is formulated as a long acting injectable for intramuscular injection.

12. The pharmaceutical composition according to claim 1, wherein the composition is formulated as a long acting injectable for subcutaneous injection.

13. A method for the treatment of a central nervous system disorder, comprising administering to a patient in need thereof a pharmaceutical composition according to claim 1, wherein said disorder is selected from the group consisting of anxiety, general anxiety disorder, social anxiety disorder, depression, refractory depression, major depressive disorder, treatment-resistant depression, psychosis, schizophrenia, sleep disorders, migraine, pain, cephalic pain, idiopathic pain, neuropathic pain, chronic pain, fibromyalgia, mood disorders, drug dependencies, opiate dependency, cocaine dependency, amphetamine dependency, alcohol dependency, withdrawal from drug or alcohol dependency, opiate overdose, binge eating disorder, obsessive-compulsive disorder (OCD), obsessive-compulsive personality disorder (OCPD), compulsive gambling disorder, compulsive eating disorder, body dysmorphic disorder, pathological grooming disorder, attention deficit-hyperactivity disorder (ADHD), attention deficit disorder (ADD), and combinations thereof.

14. The method according to claim 13, wherein said disorder is selected from the group consisting of anxiety, general anxiety disorder, social anxiety disorder, depression, refractory depression, major depressive disorder, treatment-resistant depression, psychosis, schizophrenia, pain, cephalic pain, idiopathic pain, neuropathic pain, chronic pain, mood disorders, opiate dependency, withdrawal from drug or alcohol dependency, opiate overdose, binge eating disorder, obsessive-compulsive disorder (OCD), obsessive-compulsive personality disorder (OCPD), compulsive gambling disorder, compulsive eating disorder, body dysmorphic disorder, pathological grooming disorder, attention deficit-hyperactivity disorder (ADHD), attention deficit disorder (ADD), and combinations thereof.

15. The method according to claim 13, wherein said disorder is a disorder selected from obsessive-compulsive disorder (OCD), obsessive-compulsive personality disorder (OCPD), general anxiety disorder, social anxiety disorder, compulsive gambling disorder, compulsive eating disorder, body dysmorphic disorder, pathological grooming disorder, attention deficit-hyperactivity disorder (ADHD), attention deficit disorder (ADD), and combinations thereof.

16. The method according to claim 13, wherein said disorder is a disorder selected from pain, cephalic pain, idiopathic pain, neuropathic pain, chronic pain, fibromyalgia, opiate dependency, cocaine dependency, amphetamine dependency, alcohol dependency, withdrawal from drug or alcohol dependency, and opiate overdose.

17. The method according to claim 13, wherein the method further comprises administration of an agonist or partial agonist, or inverse agonist or antagonist, of the mu-opiate, kappa-opiate, delta-opiate, and/or nociceptin/orphanin receptors.

18. The method according to claim 13, wherein the method further comprises administration of buprenorphine, methadone, naloxone or naltrexone.

19. The pharmaceutical composition according to claim 1, wherein the pharmaceutically acceptable diluent or carrier comprises a polymeric matrix.

20. The pharmaceutical composition according to claim 19, wherein the polymeric matrix comprises polylactide, poly-d,l-lactide, polyglycolide, or a poly(d,l-lactide-co-glycolide) copolymer.

21. The pharmaceutical composition according to claim 19, wherein the compound is dissolved, dispersed, or encapsulated in the polymeric matrix.

22. The pharmaceutical composition according to claim 19, wherein the compound is dissolved in an aqueous carrier.

23. The pharmaceutical composition according to claim 19, wherein the compound is dissolved in a water-miscible diluent or carrier.

24. The pharmaceutical composition according to claim 23, wherein the water-miscible diluent or carrier is an organic solvent.

* * * * *

UNITED STATES PATENT AND TRADEMARK OFFICE
CERTIFICATE OF CORRECTION

PATENT NO. : 12,173,004 B2
APPLICATION NO. : 18/451465
DATED : December 24, 2024
INVENTOR(S) : Li et al.

Page 1 of 2

It is certified that error appears in the above-identified patent and that said Letters Patent is hereby corrected as shown below:

In the Specification

Column 5, Line 43, "$CH_{5-20}alkyl$" should be changed to "$C_{5-20}alkyl$"

Column 5, Line 43, "$CH_{9-18}alkyl$" should be changed to "$C_{9-18}alkyl$"

Column 5, Line 43, "$CH_{10-16}alkyl$" should be changed to "$C_{10-16}alkyl$"

Column 5, Line 47, "$CH_{9-18}alkyl$" should be changed to "$C_{9-18}alkyl$"

Column 5, Line 48, "$CH_{10-16}alkyl$" should be changed to "$C_{10-16}alkyl$"

Column 5, Line 52, "$CH_{9-18}alkyl$" should be changed to "$C_{9-18}alkyl$"

Column 6, Lines 49 to 67, "                                                                 "

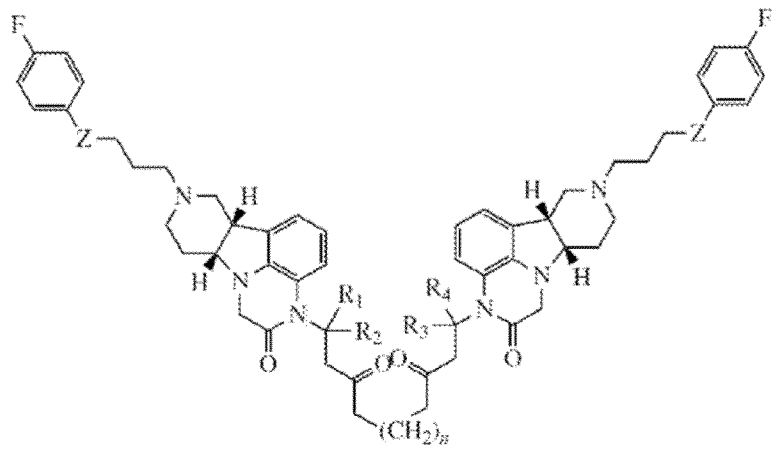

Signed and Sealed this
First Day of April, 2025

Coke Morgan Stewart
*Acting Director of the United States Patent and Trademark Office*

CERTIFICATE OF CORRECTION (continued)
U.S. Pat. No. 12,173,004 B2 should be changed to " 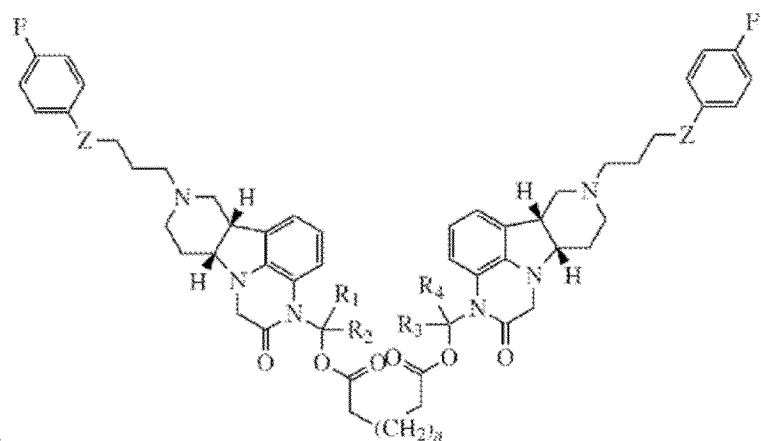 "